US006689563B2

(12) United States Patent
Preparata et al.

(10) Patent No.: US 6,689,563 B2
(45) Date of Patent: Feb. 10, 2004

(54) SYSTEM AND METHODS FOR SEQUENCING BY HYBRIDIZATION

(75) Inventors: Franco P. Preparata, Providence, RI (US); Eliezer Upfal, Providence, RI (US)

(73) Assignee: Brown University Research Foundation, Providence, RI (US)

(*) Notice: Subject to any disclaimer, the term of this patent is extended or adjusted under 35 U.S.C. 154(b) by 405 days.

(21) Appl. No.: 09/735,776

(22) Filed: Dec. 13, 2000

(65) Prior Publication Data

US 2001/0004728 A1 Jun. 21, 2001

Related U.S. Application Data

(62) Division of application No. 09/416,779, filed on Oct. 13, 1999.
(60) Provisional application No. 60/103,998, filed on Oct. 13, 1998, and provisional application No. 60/125,704, filed on Mar. 23, 1999.

(51) Int. Cl.$^7$ .................................................. C12Q 1/68
(52) U.S. Cl. ........................................................... 435/6
(58) Field of Search ................................ 435/6; 436/94

(56) References Cited

U.S. PATENT DOCUMENTS

| | | | |
|---|---|---|---|
| 5,002,867 A | 3/1991 | Macevicz | 435/6 |
| 5,202,231 A | 4/1993 | Drmanac et al. | 435/6 |
| 5,288,514 A | 2/1994 | Ellman et al. | 427/2 |
| 5,359,115 A | 10/1994 | Campbell et al. | 558/110 |
| 5,362,899 A | 11/1994 | Campbell | 558/108 |
| 5,424,186 A | 6/1995 | Fodor et al. | 435/6 |
| 5,599,695 A | 2/1997 | Pease et al. | 435/91.1 |
| 5,665,975 A | 9/1997 | Kedar | 250/573 |
| 5,681,947 A | 10/1997 | Bergstrom et al. | 536/286 |
| 5,683,881 A | 11/1997 | Skiena | 435/6 |
| 5,744,305 A | 4/1998 | Fodor et al. | 435/6 |
| 5,795,716 A | 8/1998 | Chee et al. | 435/6 |
| 5,908,745 A | 6/1999 | Mirzabekov | 435/6 |
| 5,972,619 A | 10/1999 | Drmanac et al. | 435/6 |
| 6,108,666 A | 8/2000 | Floratos et al. | 707/104 |

FOREIGN PATENT DOCUMENTS

| | | |
|---|---|---|
| EP | 0 834 575 A2 | 4/1998 |
| WO | WO 90/04652 | 5/1990 |
| WO | WO 91/07087 | 5/1991 |
| WO | WO 92/10092 | 6/1992 |
| WO | WO 93/09668 | 5/1993 |
| WO | WO 93/20242 | 10/1993 |
| WO | WO 93/22480 | 11/1993 |
| WO | WO 96/17957 | 6/1996 |

OTHER PUBLICATIONS

Arratia, R. and Reinert, G.; "Poisson Process Approximation For Repeats in One Sequence and Its Application to Sequencing by Hybridization", Proceedings: Combinatorial Pattern Matching, 7$^{th}$ Annual Symposium CPM, pp. 209–219 (Jun. 10–12, 1996).

Bains and Smith; "A Novel Method for Nucleic Acid Sequence Determination", J. Theor. Biol. 135: 303–307 (1988).

Chen et al.; ""Analogous" Organic Synthesis of Small Compound Libraries: Validation of Combinatorial Chemistry in Small Molecule Synthesis", J. Am. Chem. Soc. 116: 2661–2662 (1994).

Chetverin and Kramer; "Oligonucleotide Arrays: New Concepts and Possibilities", Bio/Technology 12:1093–1099 (Nov. 1994).

Drmanac et al.; "Sequencing of Megabase Plus DNA by Hybridization: Theory of the Method", Genomics 4: 114–128, (1989).

Frieze et al.; "Optimal Reconstruction of a Sequence From its Probes", Journal of Computational Biology, pp. 1–12 (Aug. 11, 1999).

Hudson Benoit; "An Experimental Study of SBH With Gapped Probes", Technical Report CS–99–07, Dept. of Computer Science, Brown University, Rhode Island, (Apr. 1999).

Loakes And Brown, "5–Nitroindole as an Universal Base Analogue", Nucleic Acids Research 22 (20): 4039–4043 (1994).

Loakes et al.; "3–Nitropyrrole and 5–Nitroindole as Universal Bases in Primers for DNA Sequencing and PCR", Nucleic Acids Research, 23 (13) : 2361–2366 (1995).

Nichols et al.; "A Universal Nucleoside for Use at Ambiguous Sites in DNA Primers", Nature 369: 492–493 (Jun. 9, 1994).

Pevzner et al.; "Improved Chips for Sequencing by Hybridization", Journal of Biomolecular Structure and Dynamics, 9 (2): 399–410 (1991).

Pevzner, A. Pavel; "1–Tuple DNA Sequencing: Computer Analysis", Journal of Biomolecular Structure and Dynamics 7 (1): 63–73 (1989).

Preparata et al.; "On the Power of Universal Bases in Sequencing by Hybridization", Third Annual International Conference on Computational Molecular Biology, pp. 295–301 (Apr. 11–14, 1999 Lyon, France).

Strezoska et al.; "DNA Sequencing by Hybridization: 100 Bases Read by a Non–Gel–based Method", Proc. Natl. Acad. Sci. USA, 88: 10089–10093 ( Nov. 1991).

International Search Report for PCT US 99/23944 mailed Jun. 13, 2000.

*Primary Examiner*—James Martinell
(74) *Attorney, Agent, or Firm*—Ropes & Gray LLP; Matthew P. Vincent; John D. Quisel

(57) ABSTRACT

The systems and methods described herein relate to nucleic acid probes comprising a a pattern of universal and designate nucleotides, or 'gapped' probes, and the use of sets of gapped probes in sequencing by hybridization to determine the sequence of nucleic acid sequences. The inclusion of universal nucleotides in the probes allows for efficient and rapid sequencing of longer nucleotide sequences than can be sequenced using traditional probes. The systems and methods described herein also relate to apparatus for sequencing nucleic acids which include gapped probes, as well as computer systems capable of analyzing data generated using gapped probes in such apparatus.

5 Claims, 8 Drawing Sheets

Sequence: ACTTACGTTAGCTTATG

(3,1)-Probe Spectrum:

ACT-CACG-A  AGC-A
GCT-TGTT-C
CGT-G       CTT-G
TAC-TTAG-T  TTA-T

(2,2)-Probe Spectrum:

```
TAGACCGATA    CGUTUA   ATUGUT
              CGUTUG   ATUCUT
```

Fig. 4A

```
TAGACCGATA
    CGUTUA
    CGUTUG
```

Fig. 4B

```
TAGACCGATA
       ATUGUT
       ATUCUT
```

Fig. 4C

| 95% success rate | | | | | | | | |
|---|---|---|---|---|---|---|---|---|
| (s,r)-pattern | (9,0) | (8,1) | (7,2) | (6,3) | (5,4) | (4,5) | (3,6) | (2,7) |
| random | 101 | 669 | 2179 | 4325 | 6550 | 8782 | 8852 | 4272 |
| archae | 63 | 305 | 886 | 1440 | 1741 | 1741 | 1304 | 689 |
| e.coli | 72 | 415 | 1255 | 2245 | 3142 | 3300 | 2602 | 1529 |
| haemo | 59 | 321 | 886 | 1590 | 2120 | 2227 | 1843 | 1028 |

| 90% success rate | | | | | | | | |
|---|---|---|---|---|---|---|---|---|
| (s,r)-pattern | (9,0) | (8,1) | (7,2) | (6,3) | (5,4) | (4,5) | (3,6) | (2,7) |
| random | 139 | 899 | 2524 | 5009 | 7584 | 10169 | 10249 | 4947 |
| archae | 86 | 460 | 1318 | 2358 | 3300 | 3300 | 2477 | 1255 |
| e. coli | 97 | 536 | 1607 | 3016 | 4430 | 5389 | 4252 | 2384 |
| haemo | 86 | 437 | 1136 | 2137 | 2992 | 3300 | 3016 | 1607 |

SEQUENCE: ACTTACGTTAGCTTATG

SYSTEM AND METHODS FOR SEQUENCING BY HYBRIDIZATION

REFERENCE TO RELATED APPLICATIONS

This case claims priority to U.S. application Ser. No. 60/103,998, entitled "On the Power of Universal Bases in Sequence by Hybridization" and filed Oct. 13, 1998 and U.S. application Ser. No. 60/125,704, entitled "Systems and Methods for Sequencing by Hybridization" and filed Mar. 23, 1999, and is a divisional of U.S. application Ser. No. 09/416,779 filed Oct. 13, 1999, the contents of which are herein incorporated by reference.

FIELD

The invention pertains to methods for determining the order of a set of subsequences, and more particularly, a method for determining the sequence of a series of nucleic acids by ordering a collection of probes.

BACKGROUND OF THE INVENTION

The ability to determine nucleic acid sequences is critical for understanding the function and control of genes and for applying many of the basic techniques of molecular biology. Sequencing the human genome and other model organisms was first made possible by the inventions of Sanger et. al. *PNAS* 74: 5463–5467 (1977) and Maxam et. al. *PNAS* 74: 560–564 (1977). The Sanger method has seen great advances including automation, but still only 300 to 500 bases can be sequenced under optimum conditions.

Sequencing by hybridization (SBH) is a new and promising approach to DNA sequencing which offers the potential of reduced cost and higher throughput over traditional gel-based approaches. Strezoska, et.al. *PNAS USA* 88: 10089–10093 (1991) first accurately sequenced 100 base pairs of a known sequence using hybridization techniques, although the approach was proposed independently by several groups, including Bains and Smith, *Journal of Theoretical Biology* 135:303–307 (1988); Drmanac and Crkvenjakov U.S. Pat. No. 5,202,231; Fodor et. al. U.S. Pat. No. 5,424,186; Lysov, et al. *Dokl. Acad. Sci. USSR* 303: 1508- (1988); Macevicz, U.S. Pat. No. 5,002,867; and Southern, European Patent EP 0 373 203 B 1 and IPN WO 93/22480. More recently, Crkvenjakov's and Drmanac's laboratories report sequencing a 340 base-pair fragment in a blind experiment (Pevzner and Lipshutz, 19th Int. Conf. Mathematical Foundations of Computer Science, Springer-Verlag LNCS 841 143–158 (1994)). All of the above articles and patents are incorporated herein in their entirety.

The classical sequencing by hybridization (SBH) procedure attaches a large set of single-stranded fragments or probes to a substrate, forming a sequencing chip. A solution of labeled single-stranded target DNA fragments are exposed to the chip. These fragments hybridize with complementary fragments on the chip, and the hybridized fragments can be identified using a nuclear detector or a fluorescent/phosphorescent dye, depending on the selected label. Each hybridization or the lack thereof determines whether the string represented by the fragment is or is not a substring of the target. The target DNA can now be sequenced based on the constraints of which strings are and are not substrings of the target. The surveys Pevzner and Lipshutz, 19th Int. Conf. Mathematical Foundations of Computer Science, Springer-Verlag LNCS 841 143–158 (1994) and Chetverin and Kramer *Bio/Technology* 12: 1093–1099 (1994) give an excellent overview of the current state of the art in sequencing by hybridization, biologically, technologically, and algorithmically.

Sequencing by hybridization is a useful technique for general sequencing, and for rapidly sequencing variants of previously sequenced molecules. Furthermore, hybridization can provide an inexpensive procedure to confirm sequences derived using other methods.

The most widely used sequencing chip design, the classical sequencing chip C(k), contains all $4^k$ single-stranded oligonucleotides of length k. In C(8) all $4^8$ =65,536 octamers are used. The classical chip C(8) suffices to reconstruct 200 nucleotide-long sequences in only 94 of 100 cases (Pevzner, et.al. *J. Biomolecular Structure and Dynamics* 9: 399–410 (1991)), even in error-free experiments. Unfortunately, the length of unambiguously reconstructible sequences grows slower than the area of the chip. Thus, such exponential growth of the area inherently limits the length of the longest reconstructible sequence by classical SBH, and the chip area required by any single, fixed sequencing array on moderate length sequences will overwhelm the economies of scale and parallelism implicit in performing thousands of hybridization experiments simultaneously when using classical SBH methods.

Other variants of SBH (including nested-strand SBH (Rubinov and Gelfand *J. Computational Biology* (1995) and positional SBH (Broude, Sano, Smith and Cantor, *PNAS* (1994)) have been proposed to increase the resolving power of classical SBH, but these methods still require large arrays to sequence relatively few nucleotides.

The algorithmic aspect of sequencing by hybridization arises in the reconstruction of the test sequence from the hybridization data. The outcome of an experiment with a classical sequencing chip C(k) assigns to each of the $4^k$ strings a probability that it is a substring of the test sequence. In an experiment without error, these probabilities will all be 0 or 1, so each k-nucleotide fragment of the test sequence is unambiguously identified.

Although efficient algorithms do exist for finding the shortest string consistent with the results of a classical sequencing chip experiment, these algorithms have not proven useful in practice because previous SBH methods do not return sufficient information to sequence long fragments. One particular obstacle inherent in this method is the inability to accurately position repetitive sequences in DNA fragments. Furthermore, this method cannot determine the length of tandem short repeats, which are associated with several human genetic diseases (Warren S T, *Science* 1996; 271:1374–1375). These limitations have prevented its use as a primary sequencing method.

Additionally, sequencing by hybridization has so far failed to perform near the theoretical maximum efficiency. For example, the classical probing scheme uses a complete set of all $4^k$-nucleotide probes, wherein k is the length of each probe sequence. The set of hybridized probes is then used to construct a directed graph, either a Hamiltonian path or its equivalent Eulerian path. Probabilistic analysis and empirical evidence confirmed that using this method, k-nucleotide probes were adequate to reliably reconstruct sequences of length proportional only to the square root of $4^k$, rather than to $4^k$, as information theory predicts. Improvements to this algorithm (e.g., Skiena, U.S. Pat. No. 5,683,881, incorporated herein by reference) have been reported, but the maximum efficiency has been elusive.

A more efficient strategy for sequencing genes by hybridization would be a tremendous boon to the biotechnology industry. For example, the tremendous potential utility of genomic sequencing projects is directly restrained by the speed of the sequencing process itself. Methods which increase the speed and efficiency of DNA sequencing proportionally increase the speed at which such projects can unlock the secrets of evolution and molecular biology.

SUMMARY OF THE INVENTION

The systems and methods described herein relate to the sequencing of nucleotide sequences using probes comprising a pattern of universal and designate nucleotides. Such probes are referred to herein as 'gapped probes' to reflect the sequence gaps created by the universal nucleotides. A universal nucleotide, as the term is used herein, describes a chemical entity which, when present in the probe, will engage in a base-pairing relationship with any natural nucleotide. Exemplary universal nucleotides include 5-nitroindole and 3-nitropyrrole, although other universal nucleotides useful for the systems and methods described herein will be known to those of skill in the art. A universal nucleotide is represented herein as U, and a designate nucleotide, e.g., A, C, G, or T, is represented as X.

Although the pattern may comprise any sequence of designate and universal nucleotides, in certain systems, the pattern is an iterative pattern, i.e., a pattern which alternates a predetermined number of universal nucleotides with a predetermined number of designate nucleotides. Exemplary gapped probes may be defined in terms of the two variables s and r, wherein s represents the number of nucleotides in a designate nucleotide sequence of the probe, and r represents the number of iterations in the pattern, each iteration of length s and comprising a string of (s-1) universal nucleotides followed by a single designate nucleotide. For example, an (s,r)-probe wherein s is 2 and r is 3, i.e., a (2,3)-probe, would comprise the pattern XXUXUXUX. The contiguous sequence of designate nucleotides in a gapped probe as described herein is referred to as the root. In the exemplary probe above, the root is XX. The length of the root of a gapped probe as described herein is represented by the variable s. A designate nucleotides, or sequence of designate nucleotides, following the first string of one or more universal nucleotides following the root is referred to herein as the first segment. In the exemplary probe above, the first segment has been underlined ($\underline{X}$). A designate nucleotides, or sequence of designate nucleotides, following a string of one or more universal nucleotides following the first segment is referred to herein as the second segment. In the exemplary probe above, the second segment has been underlined twice ($\underline{\underline{X}}$). Further segments are numbered in an analogous manner. The last designate nucleotide in the probe, typically the last nucleotide in the probe, is referred to herein as the last segment. The terms employed herein are provided to describe with clarity the exemplary gapped probe XXU$\underline{X}$U$\underline{\underline{X}}$UX, given above, wherein the root is followed by a first and last segment. However, it will be understood that in other embodiments, the contiguous sequence that forms the probe can have an alternate pattern, such as for example, wherein the root occurs within the middle, or generally the middle, of the sequence, or alternatively, when the root occurs at the end of the sequence. These alternate probe embodiments can similarly be employed for sequencing, and the techniques disclosed herein for employing these probes to order a Spectrum of hybridized probes, can be practiced with any of these probe embodiments.

The systems and methods described herein further pertain to sequencing chips carrying a set of gapped probes. A set of gapped probes, as the term is used herein, refers to a collection of probes having the same generic probe sequence, e.g., at least ten instances of the generic probe sequence. A generic probe sequence describes a pattern of designate and universal nucleotides, e.g., XXXXUUXUXX. An instance of a generic probe sequence is a sequence of designate and universal nucleotides which conforms to the pattern of the generic probe sequence, e.g., TCTAUUGUCG and GTATUUCUAG are instances of the generic probe sequence XXXXUUXUXX. In certain embodiments, a set of gapped probes comprises probes representing every instance of the designate nucleotides of the generic probe sequence.

The systems and methods described herein also relate to a process for sequencing nucleic acid sequences using gapped probes. Such a process may include providing a set of gapped probes of length k wherein the designate nucleotides vary among the set in a predetermined fashion and wherein the generic probe sequence requires a designate nucleotide at the $m^{th}$ position and the $k^{th}$ position, determining the spectrum of probes in the set of probes which hybridize with a test sequence, analyzing the spectrum of probes, and determining the sequence of the test sequence. The process may further include attaching a primer to the test sequence. Analyzing the spectrum of probes may comprise selecting probes from the spectrum whose first k-1 designate nucleotides correspond to the last k-1 designate nucleotides of the probing pattern positioned at the end of the growing sequence, matching these probes with the growing sequence to determine the next nucleotide in the growing sequence, and repeating the steps of selecting and matching until matching is no longer possible. Analyzing the spectrum of probes may further comprise selecting probes from the spectrum whose first m-1 nucleotides correspond to the last m-1 nucleotides of the growing sequence, matching these probes with the growing sequence to determine the next nucleotide, and repeating the steps of selecting and matching until conclusive matching is no longer possible. Analyzing the spectrum of probes may further comprise selecting a first probe, selecting probes from the spectrum which have a root of length s whose first s-1 nucleotides correspond to the last s-1 nucleotides of the first probe, matching these probes with the growing sequence to determine the next nucleotide, and repeating the steps of selecting and matching until conclusive matching is no longer possible.

Optionally, if a step of matching provides two or more possibilities for the next nucleotide, two or more growing sequences may be established corresponding to each of the possibilities for the next nucleotide. These alternate sequences may then be subjected to the above analysis, whereby the incorrect sequences may terminate rapidly as being unsupported by the spectrum.

The systems and methods described herein further comprise a computer program capable of analyzing a spectrum of probes comprising a natural nucleotide sequence and a pattern of universal and natural nucleotides to determine the sequence of the test sequence, e.g., by the method described above, and a disk, CD, or other storage device which contains such a program.

BRIEF SUMMARY OF THE FIGURES

The following figures depict certain illustrative embodiments of the invention in which like reference numerals refer to like elements. These depicted embodiments are to be understood as illustrative of the invention and not as limiting in any way.

FIG. 2 presents sample spectra obtained using probes as described herein.

FIG. 4 illustrates the evaluation of the spectrum for different extensions.

Figure 1:
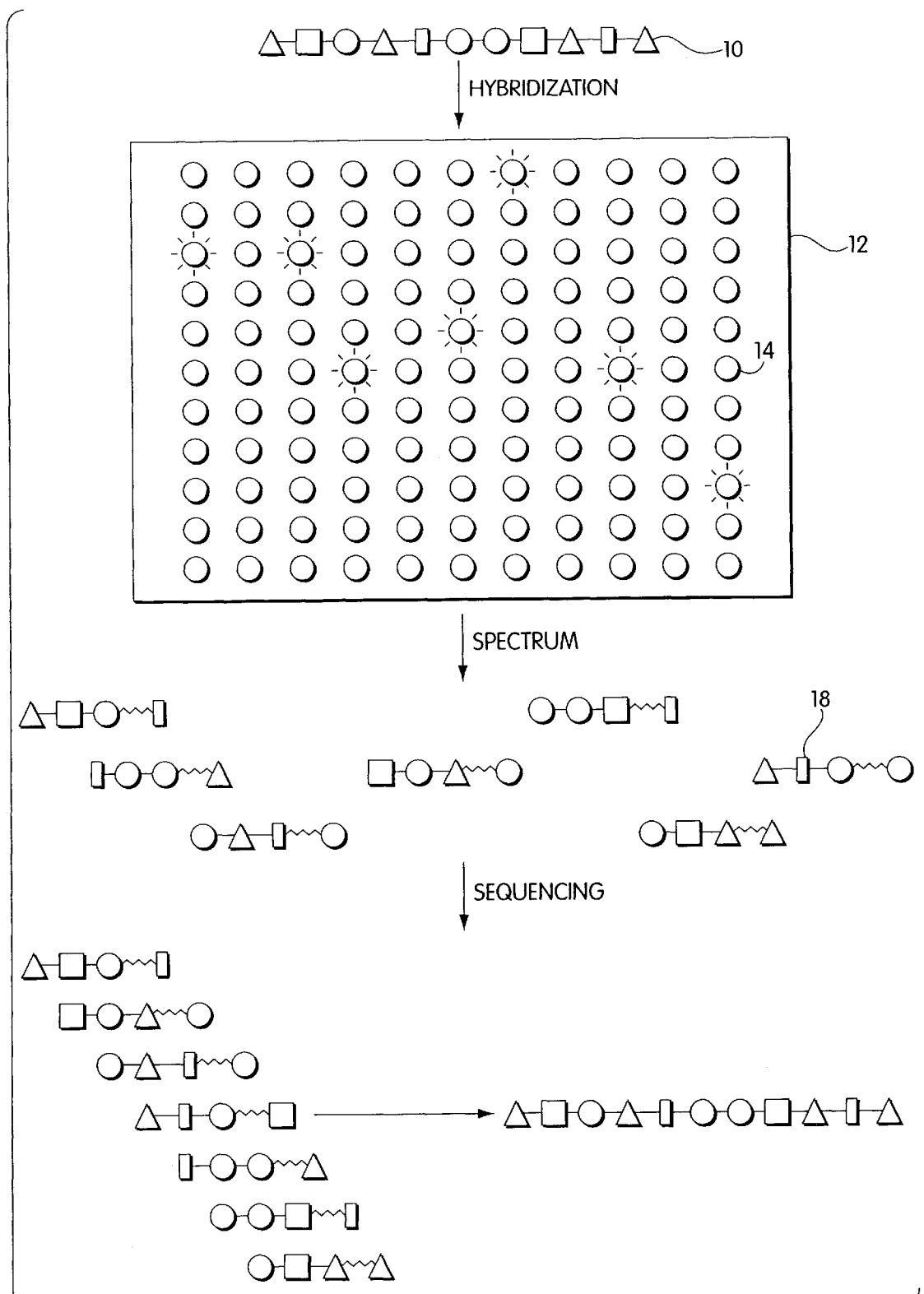
FIG. 1 schematically depicts a general method for sequencing using universal nucleotides.

DETAILED DESCRIPTION OF THE ILLUSTRATED EMBODIMENTS (i) Overview

The description below pertains to several possible embodiments of the invention. It is understood that many variations of the systems and methods described herein may be envisioned by one skilled in the art, and such variations and improvements are intended to fall within the scope of the invention. Accordingly, the invention is not to be limited in any way by the following disclosure of certain illustrative embodiments.

In general, the systems and methods described herein relate to a method for sequencing nucleotide sequences using oligonucleotide probes, referred to herein as "gapped probes". The gapped probes each comprise a sequence of "designate nucleotides" and "universal nucleotides" arranged in the probe sequence with a predefined periodicity. A "universal nucleotide", as the term is used herein, describes a chemical entity which, when present in the probe, will engage in a base-pairing relationship with any natural nucleotide (e.g., deoxyadenosine (A), deoxythymidine (T), deoxycytidine (C) and deoxyguanosine (G)). Exemplary universal nucleotides include 5-nitroindole (Loakes, D. and Brown, D. M. *Nucleic Acids Research* 1994, 20:4039–4043) and 3-nitropyrrole (U.S. Pat. No. 5,681,947 to Bergstrom, incorporated herein by reference), although other universal nucleotides will be known to those of skill in the art. A "designate nucleotide", as the term is used herein, refers to a naturally occurring nucleotide, e.g., A, T, C, or G, or an analog thereof which has base-pairing properties similar to or preferably more selective than, a naturally occurring nucleotide. Thus, the probe will include regions of designate nucleotide(s) which, under stringent hybridization conditions, selectively base-pair by A-T or G-C pairing or the like, and regions of universal nucleotides which display degeneracy in, or substantially no, selectivity in base-pairing.

The use of probes having universal nucleotides allows each probe to contribute to the sequencing process in more than one way, thereby permitting the efficient sequencing of a nucleotide sequence using a smaller number of probes than is possible using conventional probes consisting entirely of natural nucleic acids. In particular, we demonstrate herein that the use of probes with defined patterns of gaps can permit the attainment of asymptotically optimal efficiencies in sequencing-by-hybridization methods. The subject method does not require reconstructions of a sequence by Euler path processes or other such complex graph-theoretic solutions. This apparent paradox, as described below, is resolved by the observation that our proposed gap structure for the probes trivializes the Euler path identification problem, generally guaranteeing with extremely high probability that the Euler path reduces to a simple path, e.g., in a virtual $\Theta(k^2)$-gram de Bruijn graph. The subject method permits the attainment of the information-theoretic upper bound for SBH techniques.

The intuition behind our method is as follows. The inadequacy of such classical methods as described above is due to the fact that, as the length of the target sequence grows, the size of the spectrum correspondingly grows, and the ensuing de Bruijn graph, which characterizes the process, may contain more than one Eulerian path. The difficulty is that, although each node has as many incoming as outgoing edges, for a node with more than one incoming edge (branching node) there is no general way to associate an incoming edge with a unique outgoing edge, thereby engendering ambiguity. To avoid this shortcoming, our intuition was the adoption, for the same number of designate nucleotides, of "gapped" probes, which, in a way, can provide a "bridge" around branching nodes.

In one illustrative embodiment, our method uses a family of probes with a well defined periodic pattern of gaps, which we name (s,r)-probes. Denoting by $Z^f$ the f-fold repetition of a string Z, such probes have the form $X^s(U^{s-1}X)^r$ where X is selected from among the 4 standard DNA bases (A,C,G, and T) and U is the universal base. For example, a (4,3)-probe has the form:

XXXXUUUXUUUXUUUX.

Technically we view an (s,r)-probe as having s(®+1) symbols, r(s−1) of them being universal, i.e., capable of matching any nucleotide. Since there are s+r positions with an X symbol in each (s,r)-probe, the set of (s,r)-probes has exactly $4^{r+s}$ members. Examples of spectra for two different gapped probe patterns are given in FIG. 2.

The fundamental operation of sequence reconstruction is extension, the addition of one extra nucleotide symbol to the currently reconstructed sequence a. To execute an extension we search in the spectrum for all probes whose first r(s+1)−1 symbols match the last r(s+1)−1 symbols of a (there is at least one such probe). If there is only one such probe, then the extension is unambiguous and we append the rightmost symbol of the probe to the right of a. Otherwise, there may be more than one extension (ambiguous extension). An ambiguous extension occurs if and only if it is confirmed by additional r probes, to be placed at shifts of s, 2s, . . . , rs positions with respect to the first probe. The probes supporting the ambiguous extension may arise from a single segment of the target sequence; enormously more probable, however, is the event that these probes may arise from (®1) independent positions in the target sequence. It is intuitively clear, and is supported by a nontrivial probabilistic analysis, that, for fixed k, the likelihood of an ambiguous extension decreases exponentially in r, thereby enabling the (s, r)-probes to realize the information-theoretic potential of SBH, i.e., the reliable reconstruction of sequence of length proportional to $4^k$.

Figures 5, 6:
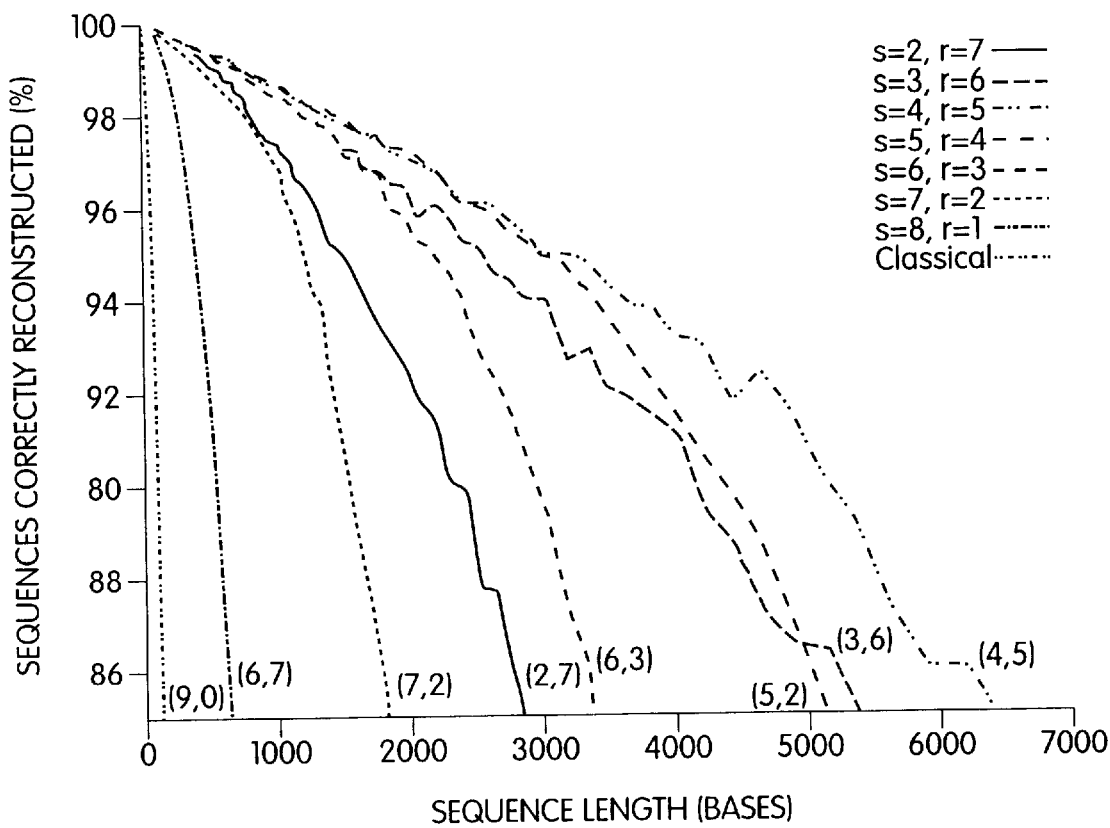
FIG. 5 depicts test results comparing the sequencing of DNA using various probes as described herein with the sequencing of DNA using conventional probes.
FIG. 6 presents the lengths of sequences that can be sequenced using gapped probes as a function of the generic probe sequence and the source of the test sequence.

Our formal analysis, as described in greater detail below, has been accompanied by extensive simulations both on artificial data (i.e., computer-generated target sequences consisting of independent and identically-distributed nucleotides) and on real data obtained from the ENTREZ Retrieval System (the genomes of *Haemophilus influenzae, Escherichia coli,* and *Methanobacterium thermoautrophicum*). For any chosen length m, the artificial sequences (referred to as "random") are produced by a random-number generator, while the natural sequences are disjoint substrings of the published genomes. Although, for a given pair (s, r), more sophisticated algorithms can achieve the reconstruction of target sequences of substantially greater length, for comparative purposes we have conducted extensive experimentation with an extremely simple reconstruction algorithm, which, for sequences of a chosen length m, very conservatively declares failure at the detection of the first ambiguous extension. Typical results of the simulations are reported in FIG. 5 and in FIG. 6 for the value k=9, which is representative of current technology. Plotted in FIG. 5 is the frequency of successful reconstruction as a function of m for the possible choices of the pair (s, r) (note that the (s, r) pairs (9,0) and (1,8) denote the same probe design). In FIG. 6, we display the results for the confidence levels 0.9 and 0.95: a displayed entry is the largest sample value for which reconstruction has been achieved with a frequency not smaller than the corresponding confidence level. Note that, due to the constrained randomness of natural sequences, their performance is inferior to that of artificial maximum-entropy sequences. However, the ratio of the performances of the best (s, r) selection and of the standard method (k, 0), is of the same order of magnitude in all test cases.

In one aspect, the subject gapped oligonucleotides are used to determine the identity, e.g., sequence, of a nucleic acid sample. In general, the present invention provides method for sequencing a segment of a nucleic acid comprising the steps of:

a) combining:
  i) a substrate comprising a library of positionally distinguishable gapped probes capable of hybridizing with defined oligonucleotide sequences; and
  ii) a test nucleic acid;
under hybridization conditions wherein gapped probes of the library form high-fidelity matched duplex structures with complementary subsequences of the test nucleic acid; and b) determining which of the gapped probes specifically hybridized with subsequences in the target polynucleotide. Detecting the positions which bind the target sequence would typically be through a fluorescent label on the test nucleic acid. Although a fluorescent label is probably most convenient, other sorts of labels, e.g., radioactive, enzyme linked, optically detectable, or spectroscopic labels may be used. Other detection techniques are described below. Because the gapped probes are positionally defined, the location of the hybridized duplex will directly translate to the sequences which hybridize. Thus, analysis of the positions provides a collection of subsequences found within the target sequence.

In certain embodiments of the subject method, it further comprises assembling a nucleotide sequence for the test nucleic acid based on the gapped probes which specifically hybridized with subsequences in the target polynucleotide. For example, such a step may include collating said gapped probes to determine the overlaps of said known sequences to determine the sequence of the test nucleic acid.

A salient feature of the subject sequencing-by-hybridization process is based upon the ability to synthesize a large number (e.g., to virtually saturate) of the possible overlapping sequence segments in the gapped probe library, and distinguishing those probes which hybridize with fidelity from those which have mismatched bases, and to analyze a highly complex pattern of hybridization results to determine the overlap regions.

In other embodiments, the invention provides methods for sequencing a nucleic acid, the method comprising the steps of:

a) preparing a plurality of gapped probes;
b) positionally attaching each of the probes to one or more solid phase substrates, thereby producing substrates of positionally definable gapped probes;
c) combining the substrates with a test nucleic acid whose sequence is to be determined; and
d) determining which of the gapped probes specifically hybridize with subsequences in the test nucleic acid.

Although most directly applicable to sequencing, the present invention is also applicable to fingerprinting, mapping, and the like.

According to one aspect, the invention provides a method for forming a plurality of oligonucleotide sequences by sequential addition of reagents comprising the step of serially protecting and deprotecting portions of the plurality of polymer sequences for addition of nucleotides using a binary synthesis strategy to provide a variegated library of gapped probes.

The present invention also provides a means to automate sequencing manipulations. The automation of detection and analysis steps minimizes the need for human intervention. This simplifies the tasks and promotes reproducibility.

The present invention also provides a composition comprising a plurality of positionally distinguishable gapped probes attached to a solid substrate, the oligonucleotides preferably being of a preselected length and collectively representing substantially all possible sequences of the same generic probe sequence. Usually the oligonucleotides are all attached to a single solid substrate. In preferred embodiments, an individual substrate, such as a chip, includes a library of at least 256 different oligonucleotide sequences, and more preferably at least 1024, 4096, 16384, or even 65536 or more different oligonucleotide sequences. When provided in "DNA chip" embodiments, the oligonucleotides will be arrayed in regions on the substrate having a density of at least 25 regions per square centimeter.

(ii) Definitions

As used herein, the term "nucleotide n" refers to the $n^{th}$ nucleotide along a given nucleic acid segment.

"Nucleotide" is an art-recognized term and includes molecules which are the basic structural units of nucleic acids, e.g., RNA or DNA, and which are composed of a purine or pyrimidine base, a ribose or a deoxyribose sugar, and a phosphate group.

A "modified nucleotide," as used herein, refers to a nucleotide that has been chemically modified, e.g., a methylated nucleotide.

"Analogs," in reference to nucleotides, includes synthetic nucleotides having modified base moieties and/or modified sugar moieties, e.g., as described generally by Scheit, Nucleotide Analogs (John Wiley, New York, 1980). Such analogs include synthetic nucleotides designed to enhance binding properties, reduce degeneracy, increase specificity, and the like. In the methods described herein, n designates a fixed position within a single stranded overhang sequence extending from each double stranded nucleic acid segment. Preferably, nucleotide n is selected by digesting a given double stranded nucleic acid segment with a restriction enzyme, e.g., a class IIS restriction endonuclease, to generate a 5' or a 3' single stranded overhang sequence corresponding to the cut site, and n is the first or the last unpaired nucleotide in the overhang sequence.

As used herein, the term "amplification" refers to an in vitro method which can be used to generate multiple copies of a nucleic acid, e.g., a DNA duplex or single-stranded DNA molecule, its complement, or both. Amplification techniques, therefore, include both cloning techniques, as well as PCR-based amplification techniques. Preferably, the nucleic acid amplification is linear or exponential, e.g., PCR amplification or strand displacement amplification. These techniques are well known to those of skill in the art. Amplification products are compositions which include a greater number of properly ligated molecules than the number of original nucleic acid segments.

The term "oligonucleotide" as used herein includes linear oligomers of natural nucleotides or analogs thereof, as well as universal nucleotides, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine or uracil (as appropriate), and "U" denotes a universal nucleotide, unless otherwise noted. Analogs of phosphodiester linkages include phosphorothioate, phosphorodithioate, phosphoranilidate, phosphoramidate, and the like. Usually oligonucleotides of the invention comprise the four natural nucleotides and universal nucleotides; however, they may also comprise non-natural nucleotide analogs for designate nucleotide positions.

"Perfectly matched" in reference to a duplex means that the oligonucleotide strands making up the duplex form a double stranded structure with one other such that every nucleotide in each strand undergoes (Watson-Crick) basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex.

Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen binding.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)-(not C)-C-(not C)-C . . ." and the like.

As used herein, the term "complexity" in reference to a population of polynucleotides means the number of different species of molecule present in the population.

Probes contemplated by the systems and methods described herein may include any pattern of universal (U) and designate (X) nucleotides, e.g., UUXUXXUX. In certain embodiments, the pattern will be iterative, e.g., UUXXUUXXUUXX, UXUXUXUX, etc. An iterative pattern simplifies the algorithms or computations used to reconstruct the test sequence. If the length of the root of a probe is identical to the length of an iteration of the pattern, the probe may be an (s,r)-probe, as the term is used herein, wherein s refers to the length of the root, and r refers to the number of iterations in the pattern, each iteration comprising universal nucleotides and a single designate nucleotide located distal to the root in its simplest version. Thus, an (s,r)-probe has a total length of s(r+1), and comprises s+r designate nucleotides. For example, a (4,2)-probe would have the generic probe structure XXXXUUUXUUUX. A generic probe structure, as the term is used herein, refers to the sequence of designate and universal nucleotides in a probe.

(s,r)-Probes are a subset of probes referred to herein as $(s,r)^P$-probes. Integer P, as used herein, is a variable which determines the number of repetitions of each X or U in a sequence. For example, a $(4,2)^2$-probe would have the generic probe structure (XX)(XX)(XX)(XX)(UU)(UU)(UU)(XX)(UU)(UU)(UU)(XX), wherein the parentheses have been used only to elucidate the structure of the probe. $(s,r)^P$-Probes may be used with the systems and methods described herein, although for purposes of clarity, (s,r)-probes will be the focus of the examples presented below.

Many additional different probe sequences may be useful in the systems and methods described herein. For example, probes without roots, e.g., UUXXXUUXXX, may offer improved results over probes consisting entirely of natural nucleotides. Similarly, probes may have a root at the beginning, end, or middle of a probe, e.g., XXXXUUXX-UUXX or XUUUXUUUXXXX, (XUUUX)(XXXX)(XUUUX)(XUUUX). Additionally, probes which have a reversing iterative pattern, e.g., (XUUXX)(XXUUX)(XUUXX), may also be useful for the systems and methods described herein. Probes comprising a reversing iterative pattern may optionally include a root as well, e.g., (XUXU)(UXUX)(XUXU)(XXX), which may be inserted at any point in the iterative pattern.

It will be obvious to one of ordinary skill in the art that the probes may be selected to exclude patterns of nucleotides having a secondary structure which promotes hairpin formation or other self-adhesion of the probes that would inhibit hybridization with a test sequence. Additionally, choice of an appropriate universal base is an important consideration. Furthermore, appropriate hybridization conditions may be selected, as discussed in greater detail below.

The probes may be used to sequence a nucleic acid sequence by providing a set of gapped probes of length k having the same generic probe structure and determining the spectrum of probes which hybridize to a test sequence. A set of gapped probes describes an array of gapped probes wherein the designate nucleotides at different positions of the probe vary throughout the set. In certain embodiments, the set will comprise all instances of designate nucleotides which correspond to the generic probe structure of the set. Such a set is referred to herein as a complete set. The probes may be presented to a sample of the test sequence in any manner that permits the identity of binding probes to be readily determined, e.g., the probes may be bound to a solid support, such as a chip.

FIG. 1 schematically depicts one embodiment of the sequencing process. In FIG. 1, a chip 12, having a set of probes 18 affixed to the surface at nodes 14, is treated with a sample of test nucleic acid sequence 10. Sequence 10 will bind to those nodes 14 having probes 18 which are complementary to a segment of sequence 10. The set of activated nodes 14 corresponds to a spectrum of probes 18 which can then be aligned and matched to reconstruct sequence 10.

Figure 3:
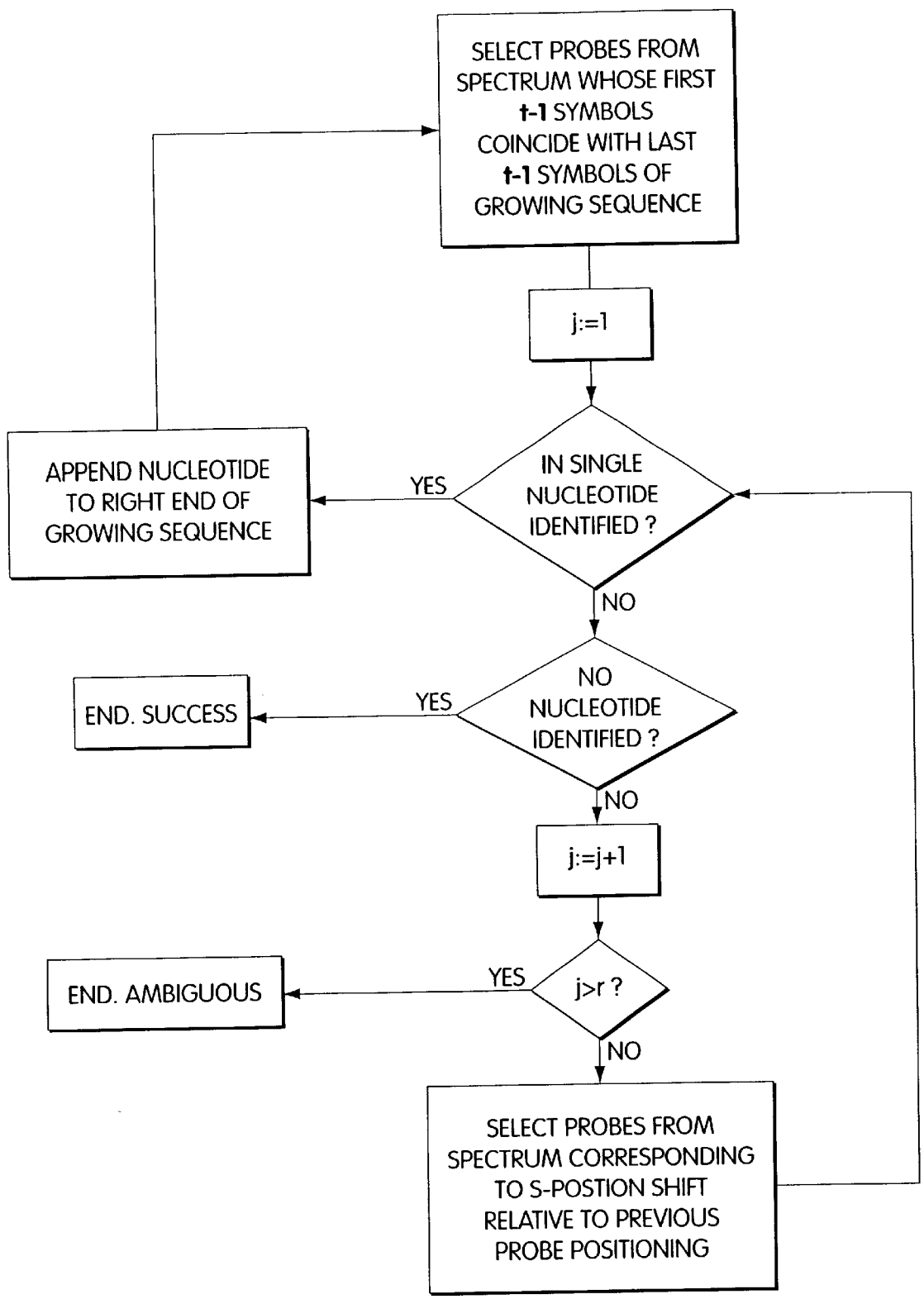
FIG. 3 depicts a method for sequencing a test sequence using probes comprising a natural nucleotide sequence and a pattern of universal and designate nucleotides.

FIG. 2 depicts a test sequence, and the derived spectra using (3,1)-probes or (2,2)-probes. The sequence of the test sequence may then be reconstructed by analyzing the members of the spectrum. FIG. 3 depicts a scheme for using a spectrum of gapped probes to reconstruct the test sequence. In this exemplary method, a subset of probes is selected from the spectrum, wherein the first k-1 nucleotides of each probe corresponds to the last k-1 probes of the growing sequence. If the last nucleotide of each probe in this subset is the same, that nucleotide is the next nucleotide in the sequence, and the process is repeated to determine the next nucleotide.

If the subset of probes provides more than one possibility for the next position in the growing sequence, then a new subset of probes is selected, wherein the next-to-last segment is aligned with the next position in the growing sequence and the preceding nucleotides correspond to the terminal nucleotides of the growing sequence. This process may be repeated with earlier segments until a single nucleotide is determined to continue the growing sequence, or the root of the probes is reached. Sequencing is complete when the spectrum cannot support further extension of the growing sequence.

FIG. 4 presents a concrete example of this technique. In this example, the growing sequence ends with the nucleotide sequence 'TAGACCGATA', and the spectrum of (2,2)-probes comprises the sequences 'CGUTUA', 'CGUTUG', 'ATUGUT', and 'ATUCUT'. Of the spectrum, only 'CGUTUA' and 'CGUTUG' can be aligned with the last five nucleotides of the growing sequence, resulting in both A and G as candidates for the next nucleotide of the growing sequence. An event wherein more than one possibility exists for the next nucleotide is referred to herein as an ambiguity. When an ambiguity is encountered, the spectrum is reevaluated to by aligning the next-to-last segment with the first unknown nucleotide of the growing sequence, thereby selecting those probes whose first three nucleotides align with the last three nucleotides of the growing sequence. This reevaluation selects the probes 'ATUGUT' and 'ATUCUT'. These probes allow either G or C to be used in extending the growing sequence, again providing an ambiguity. However, by considering both ambiguities together, it is clear that only G is supported by the spectrum, because G is the only nucleotide permitted by both subsets, and the sequencing process may move forward.

FIG. 5 depicts results generated by sequencing a series of genomic nucleotide sequences of various lengths using different complete sets of (s,r)-probes wherein s+r=9, i.e., probes comprising equal numbers of designate nucleotides. The vertical axis represents the percentage of sequences of a given length which can be sequenced using a particular (s,r)-probe. In this test, a sequence is considered unsequenceable if an ambiguity arises for which both extensions are fully supported by probes in the spectrum. FIG. 6 presents the length of a sequence which can be sequenced with a success rate of 90% or 95% using a particular (s,r)-probe depending the origin of the nucleotide sequence. These results show that, for probes wherein s+r=9, random sequences are best analyzed using (3,6)-probes, while natural sequences are sequenced optimally using (4,5) probes. In all cases, gapped probes prove far superior to conventional probes, i.e., (9,0)-probes, and the best probes can sequence sequences 25 to 85 times longer than conventional probes can for s+r=9.

In further analyzing FIGS. 5 and 6, it is important to note that for all sets of (s,r)-probes wherein s+r=9, the number of probes is constant, because the number of designate nucleotides for all such probes will be 9, and the number of probes in each set will therefore be $4^9$. The lengths of different (s,r)-probes differ, however, because different values for s and r dictate the insertion of different numbers of universal nucleotides into the sequence. Thus, sequencing using gapped probes permits the sequencing of substantially longer sequences using chips of equal size than is possible with conventional probes, because the number of probes is proportional to the size of the chip required to support them. Additionally, longer probes are advantageous for solving iterative patterns in the test sequence, because such patterns may generate spectra that cannot quantify the number of iterations if the probe length is not greater than the length of an iteration.

Although the test employed in FIGS. 5 and 6 declares a sequence unsequenceable if an unresolvable ambiguity arises, such a situation may in fact be resolvable. For example, if an ambiguity arises wherein either C or T is permissible, two growing sequences may be established, one beginning in C and the other in T. Both sequences may then be analyzed as described above. If T is the actual nucleotide of the test sequence, the growing sequence which incorporated C will often fail as being unsupported by the spectrum as sequencing progresses, and sequencing will continue only with the accurate growing sequence. Such a strategy, while computationally more demanding, permits the accurate reconstruction of sequences even longer than those demonstrated in FIGS. 5 and 6, approaching the theoretical maximum efficiency.

The sequencing process can be described in a more analytical manner. For example, the (s,r)-probes can be described as having s(r+1) nucleotides, of which r(s−1) are universal nucleotides and r+s are designate nucleotides. The generic probe structure of an (s,r)-probe has the form $X^s(U^{s-1}X)^r$, and a complete set of (s,r)-probes has $4^{s+r}$ members.

The next nucleotide in a sequence is determined by searching the spectrum for all probes whose first s(r+1)−1 nucleotides match the last s(r+1)−1 nucleotides of the growing sequence a. If there is only one such probe, then the selection of the next nucleotide is unambiguous and the sequence a can be extended by the last nucleotide of that probe. If the selection is ambiguous because more than one probe matches, the spectrum of probes is reevaluated for those probes whose first rs−1 nucleotides match the last rs−1 nucleotides of the growing sequence a. It will be apparent that this reevaluation is equivalent to aligning the next-to-last segment with the next unknown nucleotide of the growing sequence. This procedure may be repeated r times, for those probes whose last s(r+1−n)−1 nucleotides match the last s(r+1−n)−1 nucleotides of the growing sequence a for all n such that $0 \leq n \leq r$. It will be apparent to those of skill in the art that no more than four probes may match the growing sequence for n=0, because the growing sequence will dictate all positions of the probe except the last, which may be any of four nucleotides. For each whole number n, a maximum of $4^{n+1}$ probes will match, because each segment beyond the segment aligned with the first unknown nucleotide contains a nucleotide not determined by the growing sequence.

The procedure above is assisted by starting with a known series of nucleotides, herein referred to as a seed, at least as long as a probe. To this end, a seed may be attached to the test sequence as a primer. Alternatively, the beginning of the sequence may be sequenced using traditional methodology. As a third option, a first probe may be selected from the spectrum at random as a starting point and the sequence may be extended in both directions, initially employing the roots of the probes in a traditional manner for the reconstruction of a seed.

An exemplary pseudocode for performing the above analysis using (s,r)-probes is presented in Table 1 below. The below pseudo code is representative of a computer program that can operate on a data processing system such as a Sun workstation running the Unix operating system. The program can configure the data processing system to operate as a system according to the invention, and specifically to operate as a system for ordering a set of subsequences.

TABLE 1

A Sequencing Process "sequence(S; $b_{(1, (r+1)s)}$)"
    This algorithm constructs the putative sequence, starting with a "seed" $b_{(1, (r+1)s)}$. It uses as a subroutine a function extend(S; q), that operates on a probe q, and returns the parameters (b, w), in which b is a specified symbol (or set of symbols) representative of the base (or bases) that can extend the putative sequence. If the extend function fails to identify a base b for extending the putative sequence, the empty symbol $\epsilon$ is returned. Additionally, the extend function returns the parameter w, which represents whether the sequencing process should continue, or terminate. The process will continue if a base b is determined for extending the putative sequence. Alternatively, the process will terminate if the process indicates that the sequence is complete or an ambiguity has been reached that needs to be resolved through another process. The values of w can have the descriptive values of "continue", "ambiguous", and "complete."

```
                //Initialize the variables;
                l ← (r+1)s;   //Set the index of the base l being
                                matched to the last base in the seed;
                u ← continue;//Initialize u to "continue";
                //While u = continue, construct the query probe q
                //designed to extract from the spectrum (by means of
                //function extend(S;q)) the probes that may extend the
                //putative sequence;
                while (u = continue) do
                    q ← b(l-s(r+1) +2, q∂; // this is the current query
                              probe, consisting of the suffix of the
                              putative sequence concatenated with
                              the universal symbol ∂;
                    (b, w) ← extend(S; q); // call the extend
procedure;
                    if (w = continue)//test the value w returned by
                              //extend. If (w≠continue), then no
                              //extension occurs and the algorithm
                              //terminates.
                              then
                              b(1, l+1) ←b(1,q)b //extend sequence;
                              l ← l+1 //increment index
                    u ← w
                return (b(1,q), w) //returns either the correct extension
                              or termination information;
The Extend Procedure-This is a procedure for identifying the base b to be appended to
the putative sequence.
extend(S; q)
            M ← search(S; q)//  The Search Function searches though the spectrum S to
                          find the set M of probes that match the query q;
            if(|M| = 0)//In the case that no matches are found;
                then return (ε, complete) // return empty value to terminate the
                sequence
            else/(|M| ≥ 1)//If more than one sequence was found to match q;
                for each a ∈ M do
                    replace a with q(1,(r+1)s−1)a(r+1)s//slide the sequence
                    j ← 0//initialize j to 0
                while (|M| > 1) and (j ≤ r)do //this may iterate at most r times
                    U ← ∅//initialize U to the null set. At the end of the next loop,
                          U will give the set of possible extensions
                    for each a ∈ M do
                        q ← a(s+1,(r+1)s)δ^s
                        W ← search(S; q)
                        for each a ∈ W do
                            replace a with q(1,(r+1)s−1)a(r+1)s
                        U ← U ∪ W //Build the set U;
                    M ← U
                    j ← j + 1
```

TABLE 1-continued

```
if (|M| = 1)//If just one base is found to extend the sequence;
    then
        a ← M //select a from the set M;
        b ← a_{s(r+1-j)}//assign the base b the value a_{s(r+1) - j};
        return (b, continue)
    else //the process fails
        Σ ← ∅ // Σ, initialized to the empty set, is designed to
              contain all ambiguous extensions
        foreach a ∈ M do
            b ← a_{s(r+1-j)}
            Σ ← Σ ∪ {b}
        return (Σ, ambiguous) //   return the set of ambiguous
                                  extensions
```

For the purpose of the pseudo code, S represents the spectrum generated by the test sequence, a probe is represented by q, and δ represents a universal nucleotide. The test sequence is represented as $b_{(1,l)}$, of which $b_i$ represents the $i^{th}$ nucleotide and $b_{(i,j)}$ represents $b_i, b_{i+1}, \ldots, b_j$. The process begins with a seed, $b_{(1,(r+1)s)}$, which may itself be generated using the algorithm seed(S).

Turning now to the pseudo code of Table 1, we can see that the process begins with the function sequence that incrementally processes the sample data to determine base-by-base, the order of the sequence. To this end, the process begins by initializing the parameters l and u, wherein l represents the index of the rightmost base, and u is a control parameter that represents whether the process should continue or terminate. The process then proceeds to a while-loop wherein the function extend is called. The extend function takes as input variables S and q, wherein S represents the Spectrum being processed and q represents the probe being matched.

The extend function, also represented by pseudo code in Table 1, processes the Spectrum S to find the set M of probes that match the probe q. To this end, the extend calls the function search that identifies the members of set M. If the search function determines that matches were found, the process continues. If not, the condition if (|M|=0) tests true, and extend returns the parameter "complete" to the sequence function, causing the while-loop test condition to fail, and further sequencing to stop.

In the case where matches were found to define a set M, if the set M includes one or more members, the process replaces each member of the set M with a sequence represented by $q_{(r+1)s-1)}a_{(r+1)s}$; thereby creating a new sequence to search for within the Spectrum S. If the set M includes more than one member, and the number of segments r to the probe is greater than j, then the process creates a set W of the probes that correspond to the new sequence, and determines if the sets U and W intersect. If such an intersection is found, the base b is deemed identified and the function extend returns the base b and the control parameter "continue." Alternatively, if no intersection is found, the process continues until all segments r have been checked. If no intersection is found between the sets U and W after all segments r are processed, the process returns an empty set and the control parameter w is assigned the value "ambiguous." The sequence function while-loop then fails and the process terminates.

More powerful variants of the above pseudo code, termed supersequence and superextend, are presented in Table 2, and pseudo code for the process of sequencing in the reverse direction, using reversesequence, reversextend, and seed, is presented in Table 3. Supersequence and superextend differ functionally in that when an ambiguity is reached, multiple sequences are extended, as discussed above. Reversesequence and reverseextend function similarly to sequence and extend, and seed represents a process for establishing a seed sequence, as discussed above.

TABLE 2

```
Supersequence (S; b_{(1,(r+1)s)})
    l ← (r+1)s
    u ← continue
    while (u = continue) do
        q ← b_{(l-s(r+1)+2, l)}δ
        (b, w) ← superextend(S; q)
        if (w = continue)
            then
                b_{(1,l+1)} ← b_{(1,l)}b
                l ← l+1
                u ← w
    return (b_{(1,l)}, w)
Superextend (S; q)
    (b, w) ← extend (S; q) //b is in general a set of nucleotides //
    if (w = continue) or (w = complete)
    then
        return (b, w) // this is the "normal" action //
    else
        T ← ∅    //T is the set of the pairs (a, p) where p is the
                   current suffix of a path and a is the first
                   symbol of that path //
        for each a ∈ b do
            T ← T ∪ {(a, q_{(2,(r+1)s-1)}aδ)}
        i ← 1 //the algorithm begins the extension of the paths.
                 Counter i is the depth of the extension
                 and H is the extension bound.
                 When T becomes a singleton the
                 ambiguity disappears //
        while (i < H)or(|T|>1)do
            T' ← ∅ //T' is designed to produce the update of set
                     T//
            foreach (a,p) ∈ T do
                (c, v) ← extend (S, p)//c is in general a set of
                                        nucleotides//
                if (v ≠ complete)
                then
                    foreach d ∈ c do
                        T' ← T' ∪ {(a,p_{(2,(r+1)s-1)}d δ)}
                    //the pair of a path
                                            is updated retaining
                                            its origin//
            if(i > rs + 1)and(|T'| > 1)//for i ≤ rs + 1 both
                    correct and spurious paths are extended.
                    The algorithm checks if just one path
                    origin survives before attaining
                    the barrier H//
                then
                    U ← {b:(b,p) ∈ T'}//U is the set of distinct
                                            path origins//
                    if (|U|=1) // the extension terminates
                              successfully //
                    then
                        return (U, continue)
```

TABLE 2-continued

```
            T ← T'
            i ← i + 1
            if (|T| = 1)
                then
                    (b,p) ← T
                    return (b, continue)
                else
                    Σ ← ∅
                    foreach (b, p) ∈ T do
                        Σ ← Σ ∪ {b}
                    return (Σ, ambiguous)
```

TABLE 3

```
Reversesequence(S; b_{(1,(r+1)s)})
    l ← (r+1)s
    u ← continue
    while(u = continue)do
        q ← δb_{(1,s(r+1) - 1)}
        (b, w) ← reversextend(S; q)
        if(w = continue)
            then
                b_{(1, l+1)} ← bb_{(1, l)}
                l ← l+1
                u ← w
    return(b_{(1, l)}, w)
Reversextend(S; q)
    M ← search(S; q)
    if (|M| = 0)
        then return (ε, complete)
        else/(|M| ≥ 1)/
            foreach a ∈ M do
                replace a with a_1 q_{(2, (r+1)s)}
            j ← 0
            while (|M| > 1) and (j ≤ r) do
                U ← ∅
                foreach a ∈ M do
                    q ← δa_{(1,(r+1)s - 1)}
                    W ← search (S; q)
                    foreach a ∈ W do
                        replace a with a_1 q_{(2,(r+1)s)}
                    U ← U ∪ W
                M ← U
                j ← j + 1
            if(|M| = 1)
                then
                    a ← M
                    b ← a_{s(r+1)-j}
                    return(b, continue)
                else
                    Σ ← ∅
                    foreach a ∈ M do
                        b ← a_{s(r+1)-j}
                        Σ ← Σ ∪ {b}
                    return (Σ, ambiguous)
Seed(S)
    q ← random probe from S
    V ← {q}
    for i ← 0 to s - 1 do
        foreach a ∈ V do
            u ← a_{(2,s)} δ^{rs+1}
            W ← search(S; u)
            foreach c ∈ W do
                p ← a_{(2,(r+1)s)} δ ∨ c
                V' ← V' ∪ {p}
        V ← V'
    while(|V| > 1)do
        V" ← ∅
        foreach a ∈ V do
            (b, w) ← extend(S, a)
            if(w = continue) or (w = ambiguous)
                then
                    foreach c ∈ b do
                        p ← a_{(2,(r+1)s)} c
                        V" ← V" ∪ {p}
```
</br>

TABLE 3-continued

```
        V ← V"
    q ← V
    return q
```

Figure 7:
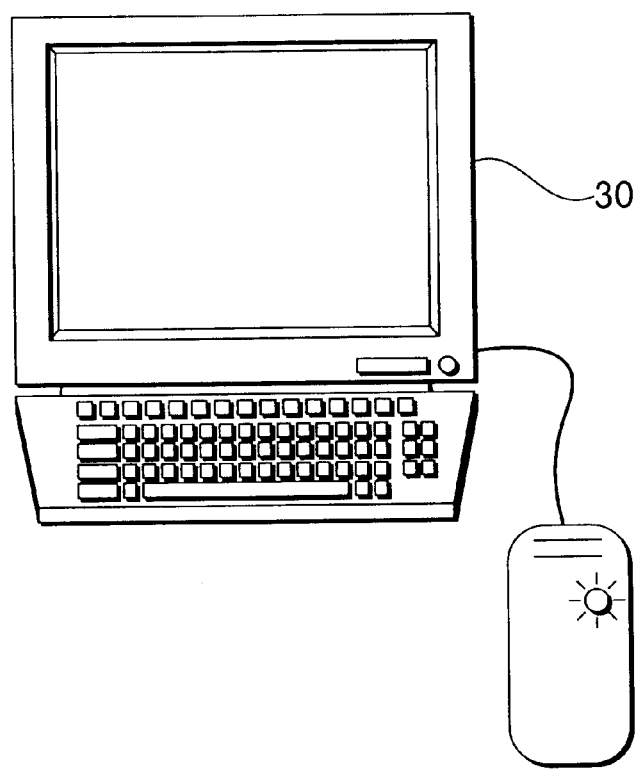
FIG. 7 depicts a computer system as described herein.
Figure 8:
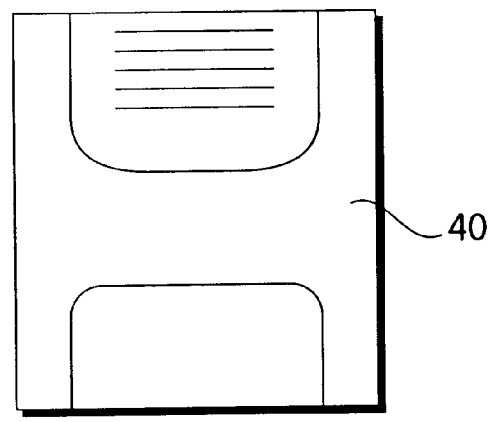
FIG. 8 depicts a disc as described herein.
Figure 9A:
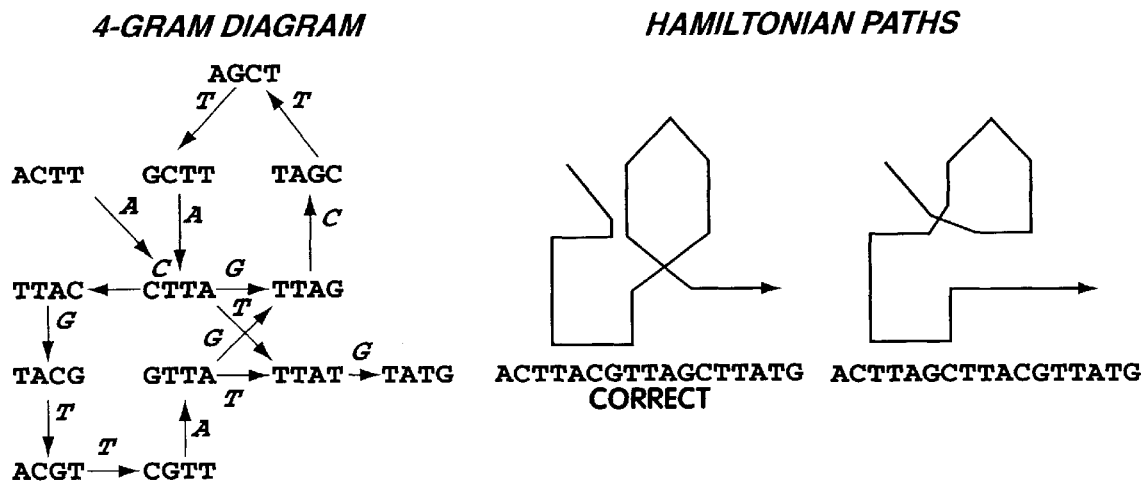
FIG. 9 illustrates (a) Hamiltonian and (b) Eulerian paths in the graph associated with a given target sequence. Both paths provide ambiguous reconstructions.
Figure 9B:
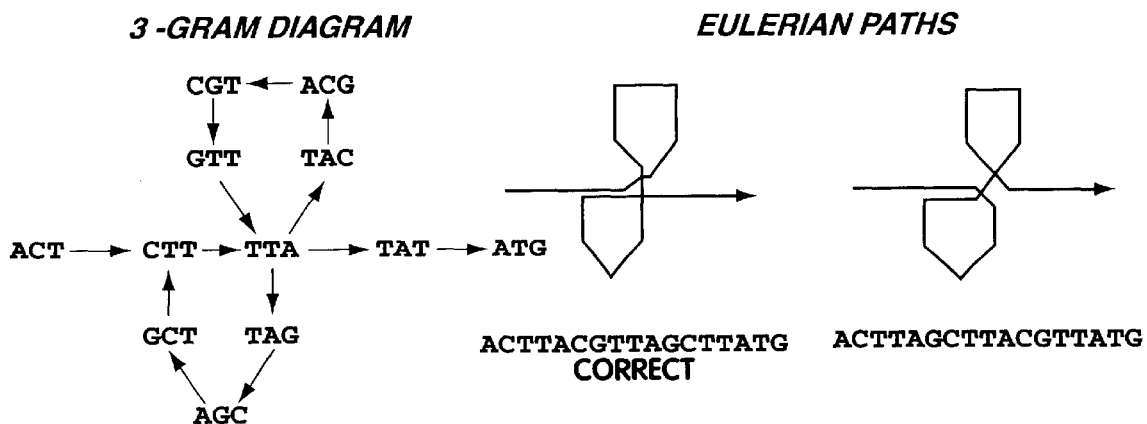
Figure 10:
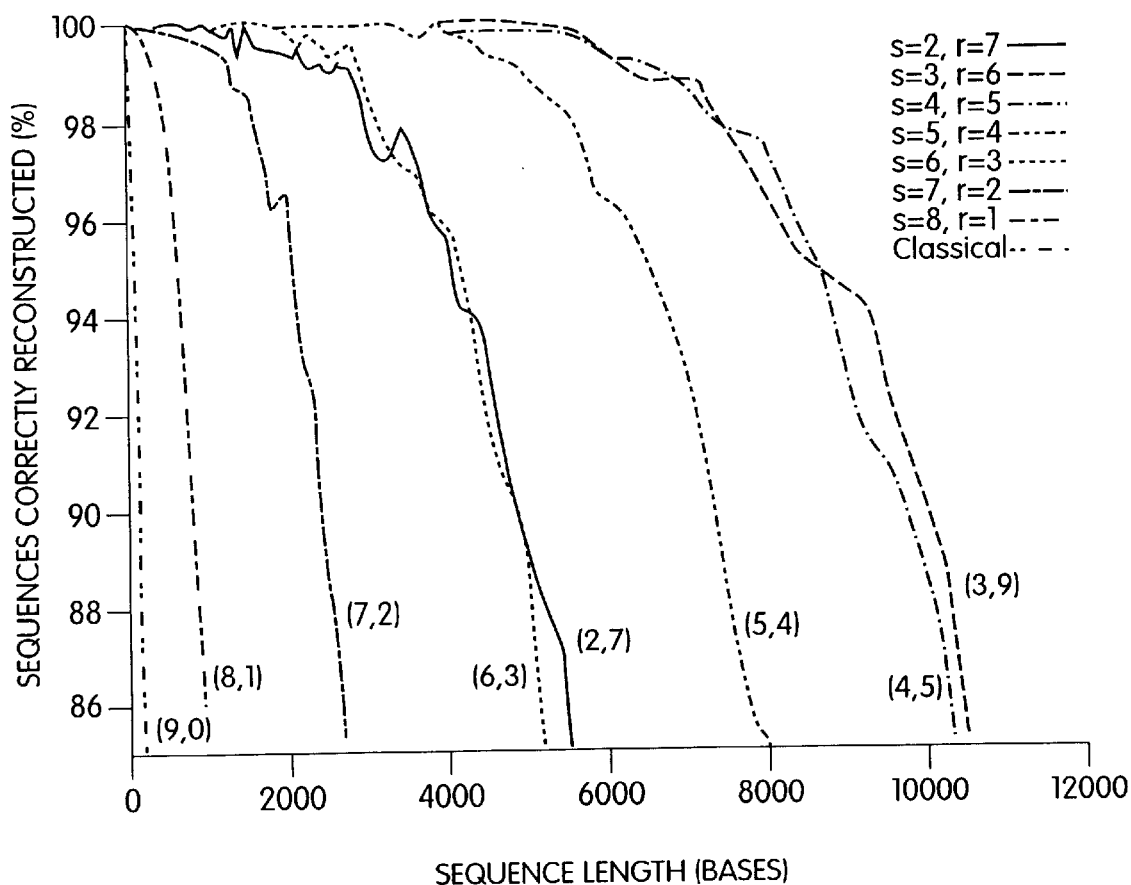
FIG. 10 depicts test results comparing the sequencing of random nucleotide sequences using various probes as described herein with sequencing using conventional probes.

One embodiment of the systems and methods described herein is a computer system configured to sequence a nucleotide sequence by analyzing a spectrum generated according to the systems and methods described herein, e.g., by executing a computer program in a computer language, e.g., Fortran, C, Java, etc., based upon the pseudocode of Table 1. An embodiment of such a computer system 30 is depicted in FIG. 7. In an additional embodiment, the systems and methods described herein relate to a disk, CD, or other permanent computer-readable storage medium that encodes a computer program capable of reconstructing a nucleotide sequence by analyzing a spectrum generated using gapped probes, such as a program based on the pseudocode of Table 1. An exemplary disk 40 is depicted in FIG. 8.

(iii) Exemplary embodiments

In principle, the making of a substrate having a positionally defined matrix pattern of all possible gapped probes of a given length and periodicity involves a conceptually simple method of synthesizing each and every different possible oligonucleotide, and affixing them to a definable position. Oligonucleotide synthesis is presently mechanized and enabled by current technology, see, e.g., Pirrung et al. (1992) U.S. Pat. No. 5,143,854; and instruments supplied by Applied Biosystems, Foster City, Calif.

The subject gapped probe oligonucleotides may be single stranded and be designed for specific hybridization to single stranded tag complements by duplex formation or for specific hybridization to double stranded tag complements by triplex formation. The probes may also be double stranded and be designed for specific hybridization to single stranded tag complements by triplex formation.

A. Preparation of Substrate Matrix

The production of the collection of specific gapped probes used in the subject methods may be produced by a variety of different methods, and arrayed in a variety of different formats.

In certain embodiments, the gapped probes are synthesized by solid phase or other synthesizing system. See, for example, instrumentation provided by Applied Biosystems, Foster City, Calif. Although a single oligonucleotide can be relatively easily made, a large collection of them would typically require a fairly large amount of time and investment. For example, there are $4^{10}=1,048,576$ possible combinations for a library of gapped probes having ten designate nucleotides. Present technology allows making each and every one of them in a separate purified form, though such might be costly and laborious.

Additional techniques available in the art for generating combinatorial libraries of small organic molecules such as gapped probes without requiring a spatial array on a solid support may be found in U.S. Pat. No. 5,665,975 to Kedar; Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242).

Once the desired repertoire of possible oligomer sequences of a given length have been synthesized, this collection of reagents may be individually positionally attached to a substrate, thereby allowing a batchwise hybridization step. Present technology also would allow the possibility of attaching each and every one of these 10-mers to a separate specific position on a solid matrix. This attachment could be automated in any of a number of ways, particularly through the use of a caged biotin type linking. This would produce a matrix having each of different possible 10-mers.

A batchwise process, however, is much preferred because of its reproducibility and simplicity. Several different technologies have been proposed to fabricate oligonucleotide arrays for SBH and can be readily adapted for generating arrays of the subject gapped probes. An automated process of attaching various reagents to positionally defined sites on a substrate is provided in, for example, Pirrung et al. (1992) U.S. Pat. No. 5,143,854; Barrett et al. (1993) U.S. Pat. No. 5,252,743; and Fodor et. al. (1991) *Science* 251:767–773; each of which is hereby incorporated herein by reference.

Instead of separate synthesis of each gapped probe, these oligonucleotides are conveniently synthesized in parallel by sequential synthetic processes on a defined matrix pattern. For instance, the oligonucleotides are synthesized stepwise on a substrate at positionally separate and defined positions. Use of photosensitive blocking reagents allows for defined sequences of synthetic steps over the surface of a matrix pattern. By use of the binary masking strategy, the surface of the substrate can be positioned to generate a desired pattern of regions, each having a defined sequence oligonucleotide synthesized and immobilized thereto.

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

Another means for generating arrays of the subject gapped probes would be to use the VLSIPS technology described in Pirrung et al. (1992) U.S. Pat. No. 5,143,854. This embodiment utilizes photolithography techniques typical of the semiconductor industry to fabricate the oligonucleotide arrays. The regions for synthesis may be very small, usually less than about $100 \mu m \times 100 \mu m$, more usually less than about $50 \mu m \times 50 \mu m$. The photolithography technology allows synthetic regions of less than about $10 \mu m \times 10 \mu m$, about $3 \mu m \times 3 \mu m$, or less.

At a size of about 30 microns by 30 microns, one million regions would take about 11 centimeters square or a single wafer of about 4 centimeters by 4 centimeters. Thus the present technology provides for making a single matrix of that size having all one million plus possible oligonucleotides having 10 designate nucleotide positions. Region size is sufficiently small to correspond to densities of at least about 5 regions/cm$^2$, 20 regions/cm$^2$, 50 regions/cm$^2$, 100 regions/cm$^2$, and greater, including 300 regions/cm$^2$, 1000 regions/cm$^2$, 3,000 regions/cm$^2$, 10,000 regions/cm$^2$, 30,000 regions/cm$^2$, 100,000 regions/cm$^2$, 300,000 regions/cm$^2$ or more, even in excess of one million regions/cm$^2$.

Although the pattern of the regions which contain specific sequences is theoretically not important, for practical reasons, certain patterns will be preferred in synthesizing the oligonucleotides. The application of binary masking algorithms for generating the pattern of known oligonucleotide probes is described in the art. By use of binary masks, a highly efficient means is provided for producing the substrate with the desired, matrix pattern of different sequences. Although the binary masking strategy allows for the synthesis of all lengths of polymers, the strategy may be easily modified to provide only polymers of a given length. This is achieved by omitting steps where a subunit is not attached.

The overall length of gapped probes used in sequencing applications will be selected on criteria determined to some extent by the practical limits discussed above. For example, there will be 65,536 possible eight designate nucleotide sequences, 262,144 possible permeations of nine designate nucleotide sequences, and, if the gapped probe has 10 designate nucleotide positions, there are 1,048,576 possible instances of sequences. As the number gets larger, the required number of positionally defined nucleotides necessary to saturate the possibilities also increases. With respect to hybridization conditions, the length of the matching necessary to confer stability of the conditions selected can be compensated for. See, e.g., Kanehisa, M. (1984) *Nuc. Acids Res.* 12:203–213.

In one illustrative embodiment, the VLSIPS technology can be used to generate an arrayed library of gapped probes. In particular, VLSIPS technology allows for the very high density production of an enormous diversity of oliognucleotides mapped out in a known matrix pattern on a substrate.

By use of protective groups which can be positionally removed, or added, the regions can be activated or deactivated for addition of particular reagents or compounds. Such methodology will typically use a photosensitive protective group on a growing oligonucleotide. Regions of activation or deactivation on the substrate may be controlled by electro-optical and optical methods, similar to many of the processes used in semiconductor wafer and chip fabrication.

In particular, the photoprotective group on the nucleotide molecules may be selected from a wide variety of positive light reactive groups preferably including nitro aromatic compounds such as o-nitrobenzyl derivatives or benzylsulfonyl. See, e.g., Gait (1984) *Oligonucleotide Synthesis: A Practical Approach*, IRL Press, Oxford. For example, 6-nitro-veratryl oxycarbony (NVOC), 2-nitrobenzyl oxycarbonyl (NBOC), or α,α-dimethyl-dimethoxybenzyl oxycarbonyl (DEZ) can be used. Useful photoremovable protective groups are also described in, e.g., Patchornik (1970) *J. Amer. Chem. Soc.* 92:6333–6335; and Amit et al. (1974) *J. Organic Chem.* 39:192–196.

By use of masking technology and photosensitive synthetic subunits, the VLSIPS apparatus allows for the stepwise synthesis of oligonucleotides according to a positionally defined matrix pattern. Each oligonucleotide probe will be synthesized at known and defined positional locations on the substrate.

Related procedures are described in U.S. Pat. Nos. 5,708,153 to Dower, 5,679,773 to Holmes, and 5,744,305 to Fodor, all of which are incorporated herein by reference.

The gapped probe oligonucleotides can be arrayed by such photolithographic techniques on a silicon or other suitably derivatized substrate.

The parameters of polynucleotide sizes of both the probes and target sequences are determined by the applications and other circumstances. The length of the oligonucleotide probes may depend in part upon the limitations of the synthesis technology to provide the number of desired probes. The sequencing procedure also requires that the system be able to distinguish, by appropriate selection of hybridization and washing conditions, between binding of absolute fidelity and binding of complementary sequences containing mismatches. Thus, the length of the gapped probe is selected for a length that will allow the probe to bind with specificity to possible target sequences under the hybridization conditions.

Hybridization Conditions

The hybridization conditions between gapped probes and test nucleic acid should be selected such that the specific recognition interaction, i.e., hybridization, of the two molecules is both sufficiently specific and sufficiently stable. See, e.g., Hames and Higgins (1985) *Nucleic Acid Hybridisation: A Practical Approach,* IRL Press, Oxford. Parameters which are well known to affect specificity and kinetics of reaction include salt conditions, ionic composition of the solvent, hybridization temperature, length of oligonucleotide matching sequences, guanine and cytosine (GC) content, presence of hybridization accelerators, pH, specific bases found in the matching sequences, solvent conditions, and addition of organic solvents.

In particular, the salt conditions required for driving highly mismatched sequences to completion typically include a high salt concentration. The typical salt used is sodium chloride (NaCl), however, other ionic salts may be utilized, e.g., KCl. Depending on the desired stringency hybridization, the salt concentration will often be less than about 3 molar, more often less than 2.5 molar, usually less than about 2 molar, and more usually less than about 1.5 molar. For applications directed towards higher stringency matching, the salt concentrations would typically be lower ordinary high stringency conditions will utilize salt concentration of less than about 1 molar, more often less then about 750 millimolar, usually less than about 500 millimolar, and may be as low as about 250 or 150 millimolar.

The kinetics of hybridization and the stringency of hybridization both depend upon the temperature at which the hybridization is performed and the temperature at which the washing steps are performed. Temperatures at which steps for low stringency hybridization are desired would typically be lower temperatures, e.g., ordinarily at least about 15° C., more ordinarily at least about 20° C., usually at least about 25° C., and more usually at least about 30° C. For those applications requiring high stringency hybridization, or fidelity of hybridization and sequence matching, temperatures at which hybridization and washing steps are performed would typically be high. For example, temperatures in excess of about 35° C. would often be used, more often in excess of about 40° C., usually at least about 45° C., and occasionally even temperatures as high as about 50° C. or 60° C. or more. Of course, the hybridization of oligonucleotides may be disrupted by even higher temperatures. Thus, for stripping of targets from substrates, as discussed below, temperatures as high as 80° C., or even higher may be used.

The base composition of the specific oligonucleotides involved in hybridization affects the temperature of melting and the stability of hybridization as discussed in the above references. However, the bias of GC-rich sequences to hybridize faster and retain stability at higher temperatures can be compensated for by the inclusion in the hybridization incubation or wash steps of various buffers. Sample buffers which accomplish this result include the triethyl- and trimethylammonium buffers. See, for example, Wood et al. (1987) Proc. Natl. Acad. Sci. USA, 82:1585–1588, and Khrapko, K. et al. (1989) FEBS Letters 256:118–122.

Temperature and salt conditions along with other buffer parameters should be selected such that the kinetics of renaturation should be essentially independent of the specific target subsequence or oligonucleotide probe involved. To ensure this, the hybridization reactions will usually be performed in a single incubation of all the substrate matrices together exposed to the identical same target probe solution under the same conditions.

The rate of hybridization can also be affected by the inclusion of particular hybridization accelerators. These hybridization accelerators include the volume exclusion agents characterized by dextran sulfate, or polyethylene glycol (PEG). Dextran sulfate is typically included at a concentration of between 1% and 40% by weight. The actual concentration selected depends upon the application, but typically a faster hybridization is desired in which the concentration is optimized for the system in question. Dextran sulfate is often included at a concentration of between 0.5% and 2% by weight or dextran sulfate at a concentration between about 0.5% and 5%. Alternatively, proteins which accelerate hybridization may be added, e.g., the recA protein found in *E. coli* or other homologous proteins.

Alternatively, various substrates may be individually treated differently. Different substrates may be produced, each having reagents which bind to target subsequences with substantially identical stabilities and kinetics of hybridization. For example, all of the high GC content probes could be synthesized on a single substrate which is treated accordingly. In this embodiment, the arylammonium buffers could be unnecessary. Each substrate is then treated in a manner such that the collection of substrates show essentially uniform binding and the hybridization data of target binding to the individual substrate matrix is combined with the data from other substrates to derive the necessary subsequence binding information. The hybridization conditions will usually be selected to be sufficiently specific such that the fidelity of base matching will be properly discriminated. Of course, control hybridizations should be included to determine the stringency and kinetics of hybridization.

Detection

Interaction between the test nucleic acid and the gapped probes may be detected by a variety of techniques. Modulation of the formation of complexes can be quantitated using, for example, detectably labeled test nucleic acids, or use of a biosensor based on, for example, surface plasmon resonance or the like.

In certain embodiments of the subject method, it may include a step of labeling test nucleic acids, for example, to permit their detection on the gapped probe array. A quickly and easily detectable signal is preferred. Certain of the apparatus for detecting hybridization to oligonucleotide arrays detect a fluorescent label. Other suitable labels include heavy metal labels, magnetic probes, chromogenic labels (e.g., phosphorescent labels, dyes, and fluorophores) spectroscopic labels, enzyme linked labels, radioactive labels, and labeled binding proteins. Still other exemplary labels are described in U.S. Pat. No. 4,366,241.

The detection methods used to determine where hybridization has taken place will typically depend upon the label selected above. Thus, for a fluorescent label, a fluorescent detection will typically be used. U.S. Pat. No. 5,143,854 describes apparatus and mechanisms for scanning a substrate matrix using fluorescence detection, but a similar apparatus is adaptable for other optically detectable labels.

The detection method provides a positional localization of the region where hybridization has taken place. However, the position is correlated with the specific sequence of the probe since the probe has specifically been attached or synthesized at a defined substrate matrix position. Having collected all of the data indicating the subsequences present in the target sequence, e.g., the "spectrum" of the test nucleic acid, this data may be aligned by overlap to reconstruct the entire sequence of the target, as illustrated below.

It is also possible to dispense with actual labeling if some means for detecting the positions of interaction between the sequence specific reagent and the target molecule are available. This may take the form of an additional reagent which can indicate the sites either of interaction, or the sites of lack of interaction, e.g., a negative label. For the nucleic acid embodiments, locations of double strand interaction may be detected by the incorporation of intercalating dyes, or other reagents such as antibody or other reagents that recognize helix formation, see, for example, Sheldon, et al. (1986) U.S. Pat. No. 4,582,789. Moreover, many techniques rely on the alteration of the electronic, optical, or mechanical properties of a probe upon hybridization, as taught in U.S. Pat. Nos. 5,670,322 to Eggers et al., 5,653,939 to Hollis et al., 5,690,894 to Pinkel, et al., and 5,759,779 to Dehlinger, without the need for labels, dyes, or any other extrinsic factors.

In another embodiment, different targets may be simultaneously sequenced where each target has a different label. For instance, one target could have a green fluorescent label and a second target could have a red fluorescent label. The scanning step will distinguish sites of binding of the red label from those binding the green fluorescent label. Each sequence can be analyzed independently from one another.

Suitable chromogens will include molecules and compounds which absorb light in a distinctive range of wavelengths so that a color may be observed, or emit light when irradiated with radiation of a particular wave length or wave length range, e.g., fluorescers. Biliproteins, e.g., phycoerythrin, may also serve as labels.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, for example, dansyl chloride; fluoresceins such as 3,6-dihydroxy-9-phenylxanthhydrol; rhodamineisothiocyanate; N-1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4-(3'pyrenyl) butyrate; d-3-aminodesoxy-equilenin; 12-(9'anthroyl) stearate; 2-methylanthracene; 9-vinylanthracene; 2,2' (vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)-phenyl] maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone.

Fluorescers are generally preferred because by irradiating a fluorescer with light, one can obtain a plurality of emissions. Thus, a single label can provide for a plurality of measurable events.

Detectable signals may also be provided by chemiluminescent and bioluminescent sources. Chemiluminescent sources include a compound which becomes electronically excited by a chemical reaction and may then emit light which serves as the detectable signal or donates energy to a fluorescent acceptor. A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

In another embodiment, hybridization of the test nucleic acid to the gapped probes can be detected using surface plasmon resonance such as is currently carried out with "sensor chip" technology. See for example U.S. Pat. No. 5,485,277; Shinohara et al. (1995) *J Biochem* (Tokyo) 117:1076–1082; Nice et al. (1993) *J Chromatogr* 646:159–168; and Jonsson et al. (1991) *Biotechniques* 11: 620–627. Surface plasmon biosensors are basically sensitive refractometers that can monitor changes in the optical state of an oligonucleotide layer, in this case, a layer of gapped probes. This is accomplished, for example, by generating the gapped probe array on top of a thin metal film evaporated onto the base of a TIR prism. When TM-polarized light in the prism is incident at the proper angle to excite surface plasmons, the TM-polarized light is attenuated drastically. In the presence of a nucleic acid duplex, the thickness and surface plasmon resonance changes, thereby altering the angular position of the reflected light.

Analysis

With automated detection apparatus, the correlation of specific positional labeling is converted to the presence on the target of sequences for which the reagents have specificity of interaction. Thus, the positional information is directly converted to a database indicating what sequence interactions have occurred.

The detection method will typically also incorporate some signal processing to determine whether the signal at a particular matrix position is a true positive or may be a spurious signal. For example, a signal from a region which has actual positive signal may tend to spread over and provide a positive signal in an adjacent region which actually should not have one. This may occur, e.g., where the scanning system is not properly discriminating with sufficiently high resolution in its pixel density to separate the two regions. Thus, the signal over the spatial region may be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, may be particularly suspect and the scanning system may be programmed to more carefully scan those positions.

In another embodiment, as the sequence of a target is determined at a particular location, the overlap for the sequence would necessarily have a known sequence. Thus, the system can compare the possibilities for the next adjacent position and look at these in comparison with each other. Typically, only one of the possible adjacent sequences should give a positive signal and the system might be programmed to compare each of these possibilities and select that one which gives a strong positive. In this way, the system can also simultaneously provide some means of measuring the reliability of the determination by indicating what the average signal to background ratio actually is.

From a listing of those sequences which interact, data analysis may be performed on a series of sequences. Although the reconstruction of the sequence can be performed manually, a computer program, or dedicated hardware, will typically be used to perform the overlap analysis. A program may be written and run on any of a large number of different computer hardware systems. The variety of operating systems and languages useable will be recognized by a computer software engineer. Various different languages may be used, e.g., BASIC; C; PASCAL; etc.

Substrate Reuse

Finally, after a particular sequence has been hybridized and the pattern of hybridization analyzed, certain of the matrix substrate can be reusable and readily prepared for exposure to a second or subsequent test nucleic acids. In order to do so, the hybrid duplexes are disrupted and the matrix treated in a way which removes all traces of the test nucleic acid. For example, the matrix may be treated with various detergents or solvents to which the substrate, the gapped probes, and the linkages to the substrate are inert. This treatment may include an elevated temperature treatment, treatment with organic or inorganic solvents, modifications in pH, and other means for disrupting specific interaction. Thereafter, a second target may actually be applied to the recycled matrix and analyzed as before.

Storage and Preservation

As indicated above, the matrix will typically be maintained under conditions where the matrix itself and the linkages and specific reagents are preserved. Various specific preservatives may be added which prevent degradation. For example, if the reagents are acid or base labile, a neutral pH buffer will typically be added. It is also desired to avoid destruction of the matrix by growth of organisms which may destroy organic reagents attached thereto. For this reason, a preservative such as cyanide or azide may be added. However, the chemical preservative should also be selected to preserve the chemical nature of the linkages and other components of the substrate. Typically, a detergent may also be included.

Processes to Avoid Degradation of Oligomers

In particular, a substrate comprising a large number of oligomers will be treated in a fashion which is known to maintain the quality and integrity of oligonucleotides. These include storing the substrate in a carefully controlled environment under conditions of lower temperature, cation depletion (EDTA and EGTA), sterile conditions, and inert argon or nitrogen atmosphere.

The techniques described above may be understood by reference to the examples provided below, which are intended to exemplify the preceding discussion and are not intended to be limiting in any way.

EXAMPLE 1

In this example a probing scheme is presented that essentially achieves the information-theoretic potential of sequencing by hybridization. The method is based on a combinatorial analysis reported in [FPU99].

The inadequacy of the classical method is due to the fact that, as the length of the target sequence grows, the size of the spectrum correspondingly grows, and the ensuing graph G", which characterizes the process, may contain more than one Eulerian path. The difficulty is that, although each node has as many incoming as outgoing edges, for a node with more than one incoming edge (branching node) there is no general way to associate an incoming edge with a unique outgoing edge, thereby engendering ambiguity. To avoid this shortcoming our intuition was the adoption, for the same number of specified nucleotides, of "gapped" probes, which, in a way, can provide a "bridge" around branching nodes.

A technical difficulty is the realization of gaps, namely, of strings of universal bases. Originally, it was proposed to realize a probe with a universal base by a mixture of probes exhibiting in the chosen position all four standard bases. Recently, a much more interesting alternative has been proposed, which uses truly universal bases (such as 5-nitroindole) [LB94], that-if used in short runs-stack correctly without binding. The approach described herein is based on the deployment of universal bases.

Specifically, this method may use a family of probes with a well defined periodic pattern of gaps, which can be named (s,r)-probes. Denoting by $Z^f$ the f-fold repetition of a string Z, such probes have the form $X^s(U^{s-1}X)^r$ where X ranges over the 4 standard DNA bases (A,C,G, and T) and U is the universal base. For example, a (4,3)-probe has the form.

XXXXUUUXUUUXUUUX.

Technically the method here is view an (s,r)-probe as having s(r+1) symbols, r(s−1) of them being universal, i.e., capable of matching any nucleotide. Since there are s+r positions with an X symbol in each (s,r)-probe, the set of(s,r)-probes has exactly $4^{r+s}=4^k$ members. Examples of spectra for two different gapped probe patterns are given in FIG. 2.

The fundamental operation of sequence reconstruction is extension, i.e., the addition of one extra nucleotide (symbol) to the currently reconstructed sequence a. To execute an extension the methods search in the spectrum for all probes whose first r(s+1)−1 symbols match the last r(s+1)−1 symbols of a (there is at least one such probe). If there is only one such probe, then the extension is unambiguous and we append the rightmost symbol of the probe to the right of a. Otherwise, there may be more than one extension (ambiguous extension). An ambiguous extension is understood to occur if and only if it is confirmed by additional r probes, to be placed at shifts of s,2s, . . . , rs positions with respect to the first probe. The probes supporting the ambiguous extension may arise from a single segment of the target sequence; which is understood significantly more probable, however, is the event that these probes (referred to herein as "fooling probes") may arise from (r+1) independent positions in the target sequence. For fixed k, the likelihood of an ambiguous extension decreases exponentially in r, thereby enabling the (s,r)-probes to realize the information-theoretic potential of SBH, i.e., the reliable reconstruction of sequence of length proportional to $4^k$.

The above analysis has been accompanied by simulations both on artificial data (i.e., computer-generated target sequences consisting of independent and identically-distributed nucleotides) and on real data obtained from the ENTREZ Retrieval System (the genomes of *Haemophilus influenzae, Escherichia coli,* and *Methanobacterium thermoautrophicum*). For any chosen length m, the artificial sequences (referred to as "random") are produced by a random-number generator, while the natural sequences are disjoint substrings of the published genomes. Although, for a given pair (s,r), more sophisticated algorithms can achieve the reconstruction of target sequences of substantially greater length (only by a constant factor, however), for comparative purposes experimentation has been conducted with simple reconstruction algorithm, which, for sequences of a chosen length m, conservatively declares failure at the detection of the first ambiguous extension. Typical results of the simulations are reported in FIG. 5 and in FIG. 6 for the value k=9, which is representative of current technology. Plotted in FIG. 5 is the frequency of successful reconstruction as a function of m for the possible choices of the pair (s,r) (note that the (s,r) pairs (9,0) and (1,8) denote the same probe design). In FIG. 6, it is display the results for the confidence levels 0.9 and 0.95: a displayed entry is the largest sample value for which reconstruction has been achieved with a frequency not smaller than the corresponding confidence level. Note that, due to the constrained randomness of natural sequences, their performance is inferior to that of artificial maximum-entropy sequences. However, the ratio of the performances of the best (s,r) selection and of the standard method (k,0), is of the same order of magnitude in all test cases. The examples set forth above follow from principles in the including those set forth in [3S91] W. Bains and G. C. Smith, A novel method for DNA sequence determination. *Jour. of Theoretical Biology* (1988), 135: 303–307; [DFS94] M. E. Dyer, A. M. Frieze, and S. Suen, The probability of unique solutions of sequencing by hybridization. *Journal of Computational Biology.* 1 (1994) 105–110; [D+89] R. Drmnanac, I. Labat, I. Bruckner, and R. Crkvenjakov, Sequencing of megabase plus DNA by hybridization. *Genomics,* (1989), 4:114–128; [FPU99] A. M. Frieze, F. P. Preparata, E. Upfal, Reconstruction of a sequence from its probes. *Computational Biology,* submitted for publication (1999); [LB94] D. Loakes and D. M. Brown, 5-Nitroindole as a universal base analogue. *Nucleic Acids Research,* (1994) 22, 20: 4038–4043; [L+88] Yu. P. Lysov. V. L. Florentiev, A. A. Khorlin, K. R. Khrapko, V. V. Shih, and A. D. Mirzabekov, Sequencing by hybridization via oligonucleotides. A novel method. *Dokl. Acad. Sci. USSR,* (1988) 303:1508–1511; [P89] P. A. Pevzner, 1-tuple DNA sequencing: computer analysis. *Journ. Biomolecul. Struct. & Dynamics* (1989) 7, 1, 63–73;; P+91] P. A. Pevzner, Yu. P. Lysov, K. R. Khrapko, A. V. Belyavsky, V. L. Florentiev, and A. D. Mirzabekov, Improved chips for sequencing by hybridization. *Journ. Biomolecul. Struct. & Dynamics* (1991) 9, 2, 399–410; and [PL94] P. A. Pevzner and R. J. Lipshutz, Towards DNA-sequencing by hybridization. 19 *Symp. on Mathem. Found of Comp. Sci.,* (1994), LNCS-841, 1 43–258.

EXAMPLE 2

In a further example it is shown that the use of probes with a well defined periodic pattern of gap allows to the attainment of asymptotically optimal efficiencies (i.e., expected sequence length $\theta(4^k)$). A probe design is presented that for any k uses $4^k$ probes to sequence a target sequence of length $\theta(4^k)$. The approach does not involve the construction of an Euler path. This apparent paradox (with respect to Pevzner's characterization) is resolved by the observation that the proposed gap structure trivializes the Euler path identification problem, providing with high probability in the chosen statistical model, that the Euler path reduces to a simple path in a virtual $\theta(k^2)$-gram De Bruijn graph. Therefore, for the attainment of the information-theoretic upper bound the implementation of gapped probes is employe, i.e., the safe insertion of "universal" (don't care) bases into the oligonucleotide. The full potential of sequencing by hybridization is predicated on the reliable deployment of universal bases.

The analytical results reported here are asymptotic. To establish the validity of the approach for practical chip sizes, extensive simulations have been run for technologically feasible parameters. The simulation results, documented in [PU99], remarkedly match the analysis, and demonstrate the advantage of our probing scheme for any number of probes, and in particular for today's practical range of SBH chips with thousands to (possibly) a few millions probes.

A Sequencing by Hybridization (SBH) chip consists of a fixed number of features. Each feature can accommodate one probe. A probe is a string of symbols (nucleotides) from the alphabet A={A,C,G,T,U}, where A,C,G, and T denote the standard DNA bases and U denotes the "don't care" symbol, implemented using a universal base [LB94].

To compare the relative capabilities of different methods, it is assumed that hybridization is an error-free process, with no missing probes nor false positives.

A sequencing algorithm is an algorithm that, given a set of probes and a sequence spectrum, decides if the spectrum defines a unique DNA sequence, and, if so, reconstructs that sequence.

Since the number of probes on an SBH chip is limited by cost and by the technology, we are interested in the design of a smallest set of probes adequate for sequencing an arbitrary string of a given length.

The following simple observation gives an information-theoretic lower bound for the size of such a set:

Theorem 1 The number of probes required for unambiguous reconstruction of an arbitrary string of length m is $\Omega(m)$.

Proof. The spectrum based on t probes is a binary vector with t components, There are $2^t$ such vectors, and each can define no more that one possible sequence. Thus $4^m \leq 2^t$, or $=\Omega(m)$. □

This theorem also implies that, in the important case $t=4^k$, we have $m \leq 4^{k-\frac{1}{2}}$. Past research [P+91, DFS94, A+96] analyzed the performance of SBH chips in the context of random strings of length m, drawn uniformly at random from the set $\mathscr{A}^m$. A similar lower bound holds in that model:

Theorem 2 For any fixed probability P>0, the number of probes required for unambiguous reconstruction with probability P of a random string of length m is $\Omega(m)$.

Proof: Since the algorithm must unambiguously reconstruct $P4^m$ sequences, the number of probes t must satisfy $P4^m \leq 2^t$, or $t=\Omega(m)$.

In this paper we focus on a special pattern of probes which we name (s,r)-gapped probes and denote GP(s,r).

Definition 1 For fixed parameters s and r the set GP(s,r) of (s,r)-gapped probes consists of all probes of the form $X^s(U^{s-1}-X)^r$ where X ranges over the 4 standard DNA bases (A, C, G, and T) and U is the universal base.

Since there are s+r locations with an X symbol in each probe in GP(s,r), the set of probes GP(s,r) consists of exactly $4^{r+s}$ individual probes.

Definition 2 Two sequences are said to agree (in a chosen relative alignment) if their symbols are identical in any position in which they are both specified.

Notationally, let $a_{(i,m)}=a_1, \ldots a_m$ be the target string, and for any $1 \leq i < j \leq m$ let $a_{(i,j)}=a_p \ldots, a_j$. Given $a_{(i,j)}$ and $i < h < j$, $a_{(i,h)}$ and $a_{(h,j)}$ are respectively the (h−i+1)-prefix and the (j−h+1)-suffix of $a_{(i,j)}$. Hereafter we assume that the set of probes GP(s,r) was used to obtain a spectrum of the string $a_{(l,m)}$.

In this "basic scheme" for sequencing the string a using the spectrum information. We assume that we are given the s(r+1)-prefix of the target string.

By $b_{(1,\ldots)}$ it is denoted the putative sequence constructed by the sequencing algorithm. The procedure starts with the prefix $b_{(1,s(r+1))}=a_{(1,s(r+1))}$. At each iteration the procedure tries to extend a current putative sequence $b_{(1,l-1)}=b_1, \ldots b_{l-1}$, $l-1 \geq s(r+1)$ with a new symbol $b_l$.

To take full advantage of the GP(s,r) probes, each symbol may have to be confirmed by up to (r+1) probes in different alignments with the current putative sequence.

The extension is attempted as follows. We find the set $M_o$ of all probes in the spectrum such that the (s(r+1)−1)-prefix of each of the probes matches the (s(r+1)−1)-suffix $b_{l-s(r+1)+1, l-1}$ of the current putative sequence, with the stated convention about don't care symbols. If $M_o$ is empty, then no extension exists and the algorithm terminates. Otherwise, if $|M_o|=1$, a single extension is defined and the corresponding symbol is appended to the putative sequence. Problematic is the case $|M_o|>1$, since it suggests an ambiguous extension. Here one uses the power of the GP(s,r) probes, since an ambiguous extension is detected only if confirmed by r+1 spectrum probes, as discussed below. If these probes confirm the ambiguous extension, either they occur scattered along the target sequence (and are referred to briefly as "fooling probes") or they originate from a single substring (of adequate length). Intuitively, our approach rests on the facts that (r+1) confirmatory fooling probes are improbable, and that even more improbable is their arising from a single substring.

When $M_o$ is not a singleton, let $B_0$ be the set of the possible extensions. The verification is executed as follows. Construct the set $M_1$ of all probes in the spectrum such that their common (sr−1)-prefix matches $b_{(l-sr+1, ae-1)}$, and their (s+1)-suffix agrees, in the sense of Definition 2 and in appropriate shifts, with the probes in $M_o$. Let $B_1$ be the set of symbols appearing in the sr-th position of the probes in $M_o$. If $B_0 \cap B_1$ is a singleton, then have a unique extension to the string. Otherwise continue by constructing the set $M_2$ of the spectrum probes whose (s(r−1)−1)-prefix matches $b_{(l-s(r-1)+1, l-1)}$, and (2s+1)-suffix agrees with the probes in $M_1$. From $M_2$ construct the corresponding set $B_2$ of extensions. Again, if $B_0 \cap B_1 \cap B_2$ is a singleton, the process is done, else proceed by considering shorter prefixes of lengths s(r−2), s(r−3), s(r−4), ..., s of the spectrum probes. If $|\cap_{j=1}^i B_j| 1$ for some $i \leq r$, then we have an unambiguous extension. Other wise, in the basic scheme halt and report the current sequence (a more thorough and better performing technique will be sketched later in this paper).

The success of the above algorithm is understood to stem from the fact that up to r additional probes, appropriately aligned along the current sequence, are used to confirm the non-uniqueness of a one-symbol extension. One could try to extend the "power" of any set of probes by using various alignments with the current string. The advantage of the set GP(s,r) is that the probability of ambiguous extension in each of the alignments, with respect to a randomly generated sequence, is almost independent of the other patterns. This property is central to the analysis presented below.

In this section an analysis is presented of the performance of the simple algorithm described in the previous section when applied to a spectrum obtained using GP(s,r) probes. It is shown that the performance of this scheme approaches the information-theoretic lower bound of Theorem 2. To simplify the presentation assume again that, in addition to the spectrum, the algorithm is provided with the s(r+1)-prefix of the target sequence. This assumption can be removed without altering the performance of the sequencing scheme.

Theorem 3 For constants $\gamma > 1$ and $\beta = o(\log m)$, such that r and s are integers, let:

$$r = \frac{1}{\gamma}\log_4 m + \beta$$

$$s = \log_4 m + 1 + \gamma - r.$$

Let $\epsilon$ be the event: The algorithm fails to sequence a random string of length m using a GP(s,r) spectrum of the string. Then:

$$Pr(\epsilon) \leq 4^{-\gamma(1+\beta)}.$$

Proof.

Let $t = \{t, t_0, t_1, \ldots, t_r\}$, denote a vector of r+2 positions in the target string, and let A(t) denote the event: there are substrings in the target sequence $a_{1,m)}$ that satisfy the following relations:

$$a_{(t_0+1, t_{0+s})} = a_{(t+1, t+s)} \quad \mathcal{B}_0(t)$$

$$a_{t_0+is} = a_{t+is} \quad 2 \leq i \leq r. \quad \mathcal{C}_0(t)$$

$$a_{(t_0+(r+1)s)} \neq a_{t+(r+1)s} \quad \mathcal{D}_0(t)$$

For $1 \leq j \leq r$:

$$a_{(t_j+1, t_j+s)} = a_{(t+js+1, t+(j+1)s)} \quad \mathcal{B}_j(t)$$

$$a_{t_j+is} = a_{t_{j-1}+(i+1)s} \quad 2 \leq i \leq r. \quad \mathcal{C}_j(t)$$

Focus first on the success of the algorithm in sequencing all but the last rs symbols of the target sequence.

Claim I The algorithm fails to sequence the m−sr prefix of the target string if and only if $\exists t$ such that A(t) occurs.

Proof: Assume that the algorithm is trying to extend the current sequence $a_{(1, l-1)}$ with the next symbol $a_l$. Let $t=l-s(r+1)$. If $|B_0|>1$ is not a singleton then there is a probe in the spectrum that matches $a_{(t+1, l-1)}$ but its rightmost symbol $b \neq a_l$. Denoting by $a_{(t_o^{i+1}, t_o^{i+s(r+1)})}$ the substring of the target string that binds with that probe, conditions $\mathcal{B}_0$, $\mathcal{C}_0$ and $\mathcal{D}_0$ hold.

If $\cap_{j=0}^r B_j$ is not a singleton, then it contains both $a_l$ and b. Thus, for each j there is a probe in the spectrum, and a corresponding substring $a_{(t_j^{i+1}, t_j^{i+(r+1)s})}$ in the target sequence, such that the s-prefix of that substring matches $a_{(t+js+1, t+(j+1)s)}$, and the locations $t_j+$ is of the substring, for $2 \leq i \leq r$ match the corresponding locations (with a shift of s positions) of the substring $a_{(t_j^{-1+1}, t_j^{-1+(r+1)s})}$ as formulated in conditions $\mathcal{B}_j$ and $\mathcal{C}_j$.

□

Let $\mathcal{T}$ denote the set of all possible vectors t, i.e.:

$$|\mathcal{T}| = \binom{m}{r+2}(r+2)!. \quad (1)$$

For a given vector $t \in \mathcal{T}$, let C(t) denote the set of components of t that are within a distance 3rs from any other component of t (in the following definition $t \equiv t_{-1}$):

$$C(t) = \{j : \exists j' < j \text{ with } |t_{j'} - t_j| < 3rs\}.$$

Let $\mathcal{T}_i$ denote the set of vectors with $|C(t)|=i$, i.e.:

$$\mathcal{T}_i = \{t \in \mathcal{T} : |C(t)| = i\}.$$

Next bound the probability of a given event $\mathcal{A}(t)$. If $t \in \mathcal{T}_o$ then the r+1 probes in the definition of $\mathcal{A}(t)$ are associated with disjoint regions of the string $a_{(1, m)}$, and thus the r+1 events are independent. If $t \in \mathcal{T}_1$, then all of the $\beta$ events are still independent, and all but at most i of the C events are independent (a B event involves s+r-1 symbols (s+r for $B_0$), a C event r-1). Thus we prove:

$$Pr(\mathcal{A}(t)) = 3 \times \left(\frac{1}{4}\right)^{(r+1)s+r^2} \quad t \in \mathcal{T}_0 \quad (1)$$

and $$Pr(\mathcal{A}(t)) \leq 3 \times \left(\frac{1}{4}\right)^{(r+1)s+r^2-i(r-1)} \quad t \in \mathcal{T}_i \quad (2)$$

If $t \in \mathcal{T}_i$ then at least i of t's components are restricted to the 3rs-neighborhood of other r+1 components. Thus $$|\mathcal{T}_i| \leq |\mathcal{T}| \binom{r+1}{i} \left(\frac{3rs(r+1)}{m}\right)^i \quad (4)$$

$$\leq \binom{r+1}{i} m^{r+2} \left(\frac{3rs(r+1)}{m}\right)^i.$$

Now bound the probability of an event ($\mathcal{A}(t)$) for $t \in \mathcal{T}_i$, $i \geq 1$:

$$Pr(\exists t \notin \mathcal{T}_0 : \mathcal{A}(t)) \leq \sum_{i=1}^{r+1} \binom{r+1}{i}(3rs(r+1))^i m^{r+2-i} 3\left(\frac{1}{4}\right)^{(r+1)s+r^2-i(r-1)}$$

and $$= 3 \frac{m^2}{4^{(\gamma+1)r+s}} \sum_{i=1}^{r+1} \binom{r+1}{i} \left(\frac{3rs(r+2)4^{r-1}}{m}\right)^i = o(1).$$

(This bound makes use of the condition $\beta=o(\log m)$.)

Let I(t) be a binary variable such that I(t)=1 if and only if event $\mathcal{A}(t)$ occurs, and let $Z = \Sigma_{t \in \mathcal{T}_o} I(t)$.

Then $$Pr(\exists t \in \mathcal{T}_0 : \mathcal{A}(t)) \leq E[Z].$$

Using (1) we get $$E(Z) \leq \binom{m}{r+2}(r+2)! \times 3 \times \left(\frac{1}{4}\right)^{(r+1)s+r^2}$$

$$\leq \frac{3m^2}{4^s} \left(\frac{m}{4^{s+r}}\right)^r \leq \frac{3m^2}{4^{s 4^{(\gamma+1)r}}} \leq 3 \times 4^{-(\beta\gamma+\gamma+1)}$$

Thus, the probability that the algorithm fails to sequence all but the last rs symbols of the sequence is bounded from above by $$Pr(\exists t \notin \mathcal{T}_0 : A(t)) + Pr(\exists t \in \mathcal{T}_0 : \mathcal{A}(t)) \leq o(1) + 3 \times 4^{-(\beta\gamma+\gamma+1)} \leq 4^{-\gamma(\beta+1)}.$$

Finally, if for all $m-rs < t < m$ we do not have the event $B_o(t) \cap C_o(t) \cap D_0(t)$ the last rs symbols are uniquely determined, i.e.:

$$Pr\left(\bigcup_{j=m-rs}^{m} (B_0(t) \cap C_0(t) \cap D_0(t))\right) \leq rs 4^{-(r+s)} = o(1).$$

□

Remark The previous theorem outlines a criterion for the selection of the parameters r and s. For given $\log_4 m$ (assumed integer), in order to reduce the cost of the chip choose a small value of $\gamma > 1$, say, $\gamma=2$, To reduce the probability of failure we choose as large a value of $\beta$ as is compatible with its defining constraint (o(log m)), so that $r = \log_4 m/2 + \beta$ and $s = \log_4 m/2 + \beta$.

The procedure described and analyzed above, which involves (r+1) fooling probes shifted at regular intervals of s positions, will be briefly referred to as forward sequencing with shift s. Now observe that the same GS(s,r) spectrum, used in forward sequencing, can also be used for sequencing in reverse. Indeed, reverse sequencing using a standard pattern $X^s(U^{s-1}X)^r$ with shift 1 is trivially equivalent to forward sequencing using the reverse pattern $(XU^{s-1})^r X^s$ with shift 1. The latter can be readily shown to be equivalent to forward sequencing using the standard pattern $X^{r+1}(U^rX)^{s-1}$ with shift (r+1), to which Theorem 3 fully applies, with the simple modification of interchanging parameters r and s-1. Concluding:

Theorem 4 For constant $\gamma > 1$ and $\beta = o(\log m)$, such that r and s are positive integers, let:

$$s = 1 + \frac{1}{\gamma} \log_4 m$$

$$r = \log_4 m + 1 + \gamma - s.$$

The algorithm fails to sequence in reverse a random string of length m using the GP(s,r) spectrum of the string with probability at most $4^{-\gamma(1+\beta)}$.

The sequencing procedure outlined above requires a "seed" of length $s(r+1) = O((\log m)^2)$ symbols to "bootstrap" the process. Three solutions are offered, two biochemical and one algorithmic, to remove this requirement. The two biochemical methods are more practical.

If the SBH process is used to sequence one string of length m, the simplest solution is to synthesize a short 'primer' (a string of length $O((\log m)^2)$) and attach it to the beginning of the string, thus providing the required prefix of the target string, In most applications, however, one needs to sequence a string that is substantially longer than can be handled by SBH chips, even using our novel scheme. The standard solution is to fragment the target sequence by means of restriction enzymes to produce a collection of overlapping substrings of sizes that can be handled by the SBH method. Once each of the substrings is sequenced, standard techniques [W95] reconstruct the entire string. Since the substrings overlap, it is not necessary to sequence the beginning and the end of each substring. Still, however, one needs to provide the algorithm with a seed sequence of length $O((\log m)^2)$ for each substring of length m. This could be achieved by the following three steps: (1) Isolate a short, $O((\log m)^2)$, piece of the target sequence and sequence it using $O(\log m)^4$ solid (no gaps) probes of length 2loglogm (standard method). (2) Use GP(s,r) probes for the forward sequencing of the portion of the target from the isolated piece to (almost) the sequence end. (3) Use the same set of GP(s,r) probes for the reverse sequencing of the portion from the isolated piece to the sequence beginning.

A third approach to the construction of a "seed" selects a probe T at random from the spectrum. Such a probe is not a string of specified symbols (it has all the gaps corresponding to the "don't care's" of the probing pattern), so that it must be "filled", i.e., all unspecified positions must be filled consistently with the spectrum. This is done using the initial s-symbol solid segment of $\pi$ as the guide, namely, accepting as a possible candidate any probe whose (s−1)-prefix coincides with the homologous suffix of the initial segment of the seed, and so on, s−1 times, until a set R($\pi$) of strings of length s(r+1)+s−1=s(r+2)−1 has been obtained. Presumably, especially if m is very large and s is rather small, the size of R($\pi$) may be quite large.

Once the set R($\pi$) has been obtained, begin the forward extension process. In the general case when $|R(\pi)|>1$, each of its members is successively extended one symbol at a time by the process described earlier. In principle, only a small number (possibly, just one) of the members of R($\pi$) are actual substrings of the target sequence (are legitimate) and all the others are spurious "paths". The expected length of spurious paths is very small, so that the extension process will rapidly eliminate them and concentrate on the legitimate members of R($\pi$) (not belonging to spurious paths). Again, this approach can involve both forward and reverse reconstruction.

In the absence of ambiguous extensions, the basic scheme is adequate in reconstructing the target sequence. However, it has been observed that an ambiguous extension spawns a spurious path, for which the spectrum is very unlikely to contain confirmatory evidence. This case is addressed by a more advanced algorithm which does not halt when encountering an ambiguous extension, but rather extends both the (unknown) legitimate path and the spurious path(s), till either all but the legitimate path cannot be extended, or two branching paths with distinct origins have been both extended up to a threshold length h. Such policy is based on the expectation that a spurious path will rapidly terminate because found to be non-extensible. This policy is obviously expected to process correctly larger target sequences. Indeed, it can be shown that by choosing an appropriate value of h (and tolerating the ensuing computational overhead) the length of the target sequence which can be reliably reconstructed can be made as close to the information-theoretic upper bound ($4^{k-1}$) as desired.

Finally, to substantiate the earlier assertion that the approach trivializes the Euler path difficulties. The probability of a recurrent state is negligibly small for the chosen length m of the target sequence, so that the Euler path with very high probability degenerates to a simple path (the states being the ((r+1)s−1)-grams of the sequence, linked, where appropriate, through the shift-register relation). It can be shown, that for practical values of the parameter k, the expected number of pairs of recurrent states is less than 1.

It is also significant to compare the probabilities that an ambiguous extension is due either to (r+1) fooling probes scattered along the sequence or to a single substring of minimal length that contains them all, since their relative values is the cornerstone of our approach. These two probabilities are, respectively, $$\binom{m}{r+2}(r+2)!\frac{3}{4}\frac{1}{4^{(k-1)(r+1)}} \text{ and } \binom{m}{2}2\frac{3}{4}\frac{1}{4^{(r+1)s-1}}.$$

The first of these expressions has been previously computed (refer to the analysis of set $T_o$ in the proof of Theorem 3), while the second one is based on the fact that the two configurations coincide in their first (r+1) s−1 symbols and differ in their last one. These two probabilities become identical for r=0 (since, in this case, s=k), i.e., for ungapped probes. This illustrates in the clearest way the unique role of gaps (universal bases), in achieving the full potential of sequencing by hybridization. The processes described above arte supported by principles in the art, including [A+96] R. Arratia, D. Martin, G. Reinert and M. S. Waterman, Poisson process approximation for sequence repeats, and sequencing by hybridization, *Journal of Computational Biology* (1996) 3,425–463; [BS91] W. Bains and G. C. Smith, A novel method for DNA sequence determination. *Jour. of Theoretical Biology* (A1988), 135, 303–307; [DFS94] M. E. Dyer, A. M. Frieze, and S. Suen, The probability of unique solutions of sequencing by hybridization. *Journal of Computational Biology*, 1 (1994) 105–110; [D+89] R. Drmanac, I. Labat, I. Bruckner, and R. Crkvenjakov, Sequencing of megabase plus DNA by hybridization. *Genomics*, (1989),4, 114–128; [HPU99] B. Hudson, F. P. Preparata, and E. Upfal, An experimental study of SBH with gapped probes. Technical Report, Dept. of Comp. Sci., Brown University (in preparation), 1999; [LB94] D. Loakes and D. M. Brown, 5-Nitroindole as a universal base analogue. Nucleic Acids Research,(1994), 22, 20,4039–4043; [L+88] Yu. P. Lysov, V. L. Florentiev, A. A. Khorlin, K. R. Khrapko, V. V. Shih, and A. D. Mirzabekov, Sequencing by hybridization via oligonucleotides. A novel method. *Dokl. Accad, Sci. USSR,* (1988) 303, 1508–1511; [P89] P. A. Pevzner, 1-tuple DNA sequencing: computer analysis. *Journ. Biomolecul. Struct. & Dynamics* (1989) 7, 1, 63–73; [P+91] P. A. Pevzner, Yu. P. Lysov, K. R. Khrapko, A. V. Belyavsky, V. L. Florentieve, and A. D. Mirzabekov, Improved chips for sequencing by hybridization. *Journ, Biomolecul. Struct. & Dynamics* (1991) 9, 2, 399–410; [PL94] P. A. Pevzner and R. J. Lipshutz, Towards DNA-sequencing by hybridization. 19*th Symp. on Mathem, Found. of Comp. Sci.,* (1994), LNCS-841, 143–258; and [W95] M. S. Waterman, *Introduction to Computational Biology*. Chapman and Hall, 1995.

To experimentally validate the above approach, a thorough simulation program has been undertaken. The current plan is to assess the cost-effectiveness (in terms of running time vs. length of correctly reconstructed sequence) of several algorithms of increasing complexity. The first coded algorithm is the above-described basic scheme.

The simulation has been conducted as follows. For a fixed value of k (where k is the number of designate nucleotides in the probes, i.e., for a chip of cost $4^k$), we select all possible values of the parameter r, i.e., r=0, 1, . . . , k−2 (note that the designs GP(k, 0) and GP(1, k−1) coincide). For each such selection, increasing values of the length m are adopted. For each value of m a random number generator is used to generate a sufficiently large sample of target sequences $a_{(1,m)}$. For each such sequence a separate routine produces the spectrum, which then forms the input to the reconstruction algorithm. Once the reconstruction is completed, it is compared with the original sequence and a statistic of failures is compiled.

The results of a sample run are displayed in FIG. 1, for k=9 and various values of r. Each plotted point corresponds to a sample of size 250. The leftmost curve corresponds to the classical ungapped probes. Note that for a confidence level 95% the classical approach yields m≈100, whereas the best result of our basic method (for r=5) is m≈8800.

EXAMPLE 3

A Sequencing by Hybridization (SBH) chip consists of a fixed number of features. Each feature can accommodate one probe. A probe is a string of symbols (nucleotides) from the alphabet, $\mathcal{A}$={A,C,G,T,U}, where A,C,G, and T denote the standard DNA bases and U denotes the "don't care" symbol, implemented using a universal base [LB94].

When the SBH chip is brought in contact with a solution of the target DNA string, a probe binds to the target string if and only if there is a substring of the target that is Watson-Crick complementary to the probe (where, conventionally, any of the four bases A,C,G,T is Watson-Crick complementary to a universal base. With this convention, a probe is viewed as a string, rather than a subsequence). Biochemical labeling permits the identification of the set of probes (called the string's spectrum) that bind to the target string.

A sequencing algorithm is an algorithm that, given a set of probes and a spectrum, decides if the spectrum defines a unique DNA sequence, and, if so, reconstructs that sequence.

Since the number of features on an SBH chip is limited by the technology, in the design of a smallest set of probes adequate for sequencing an arbitrary string of a given length is of interest.

The following simple observation gives an information-theoretic lower bound for the size of such a set:

Theorem 1 The number of probes required for unambiguous reconstruction of an arbitrary string of length m is $\Omega(m)$, Proof: The spectrum based on t probes is a binary vector with t components. There are $2^t$ such vectors, and each can define no more than one possible sequence. Thus, $4^m \leq 2^t$, or $t \geq 2^m$. □ This theorem also implies that, in the important case $t=4^k$, we have $m \leq 4^{k-\frac{1}{2}}$. Past research [P+91, DFS94, A+96] analyzed the performance of SBH chips in the context of random strings of length m, drawn uniformly at random from the set $\mathcal{A}^m$. A similar lower bound holds in that model:

Theorem 2 For any fixed probability P>0, the number of probes required for unambiguous reconstruction with probability P of a random string of length m is $\Omega(m)$, Proof: Since the algorithm must unambiguously reconstruct $P4_m$ sequences, the number of probes t must satisfy $P4^m \leq 2^t$, or $t=\Omega(m)$. □

The special pattern of probes described herein are named (s,r)-gapped probes and denote GP(s,r).

Definition 1 For fixed parameters s and r the set GP(s,r) of (s,r)-gapped probes consists of all probes of the form $X^s (U^{s-1}X)^r$ where X ranges over the 4 standard DNA bases (A, C, G, and T) and U is the universal base, Since there are s+r locations with an X symbol in each probe in GP(r,s), the set of probes GP(s,r) consists of exactly $4^{r+s}$ individual probes.

Notationally, let $a_{(1,m)}=a_1, \ldots a_m$ be the target string, and for any $1 \leq i \leq j \leq m$ let $a_{(i,j)}=a_i, \ldots, a_j$. Given $a_{(i,j)}$ and =i<h≤j, $a_{(i,h)}$ and $a_{(h,j)}$ are respectively the (h−i+1)-prefix and the (j−h+1)-suffix of $a_{(i,j)}$. Hereafter assume that the set of probes GP (s,r) was used to obtain a spectrum of the string $a_{(1,m)}$.

A procedure for sequencing the string a using the spectrum information obtained from the (s,r)-gapped probes can assume the s(r+1)-prefix of the target string is given.

The procedure produces a putative sequence b which represents the reconstruction of the sequence a. It starts with the prefix $b_{(1,s(r+1))}=a_{(1,s(r+i))}$, At each iteration the procedure tries to extend a current putative sequence $b_{(1,l-1)}=b_1, \ldots, b_{l-1}$, 1−1≥s(r+1) with a new symbol $b_l$ To take full advantage of the GP(s,r) probes, use each probe in up to r different possible alignments with the current sequence.

The extension is attempted as follows. Find the set $M_0$ of all probes in the spectrum such that the (s(r+1)−1)-prefix of each of the probes matches the (s(r+1)−1)-suffix $b_{(l-s(r+1)+1,l-1)}$ of the putative sequence, with the stated convention about don't care symbols. If $M_0$ is empty, then no extension exists and the algorithm terminates. Otherwise, if $|M_0|=1$ a single extension is defined and the corresponding symbol is appended to the putative sequence. The case $|M_0|>1$ is problematic since it suggests an ambiguous extension. Here use the power of the GP(s,r) probes, since an ambiguous extension is detected only if confirmed by r+1 spectrum probes, as discussed below. If these probes confirm the ambiguous extension, either they occur scattered along the target sequence (and are referred to briefly as "fooling probes") or they originate from a single substring (of adequate length). It appears that (r+1) confirmatory fooling probes are very improbable, and that even more improbable is their arising from a single substring.

When $M_0$ is not a singleton, let $B_0$ be the set of the possible extensions. The verification is executed as follows. Construct the set $M_1$ of all probes in the spectrum such that their common (sr−1)-prefix matches $b_{(l-sr+1,l-1)}$, and their (s+1)-suffix agrees[1] with the probes in $M_0$. Let $B_1$ be the set of symbols appearing in the sr-th position of the probes in $M_0$. If $B_0 \cap B_1$ is a singleton, then have a unique extension to the string. Otherwise continue by constructing the set $M_2$ of the spectrum probes whose (s(r−1)−1)-prefix matches $b_{(l-sr+1,l-1)}$, and (2s+1)-suffix agrees with the probes in $M_1$. From $M_2$ construct the corresponding set $B_2$ of extensions. Again, if $B_0 \cap B_1 \cap B_2$ is a singleton the processes are done, else we proceed by considering shorter prefixes of lengths s(r−2), s(r−3),s(r−4), . . . , s of the spectrum probes. If $|\cap_{j=1}^{i} B_j|=1$ for some i≤r, then there is an unambiguous extension. Otherwise, in the basic scheme halt and report the current sequence. Other algorithms, may explore all branches of an ambiguous extension, in the expectation that after a small number of extensions only one branch will be supported by the spectrum.

The success of the above algorithm stems from the fact that up to r probes, appropriately aligned along the current sequence, are used to confirm the uniqueness of a one-symbol extension. One could try to extend the "power" of any set of probes by using various alignments with the current string. The advantage of the set GP(s,r) is that the probability of ambiguous extension in each of the alignments, with respect to a randomly generated sequence, is almost independent of the other patterns. This property is central to the analysis presented below.

An analysis of the performance of the algorithm described in the previous section when applied to a spectrum obtained using GP(s,r) probes is presented below. The performance of this scheme approaches the information-theoretic lower bound of Theorem 2. To simplify the presentation assume again that together with the spectrum the algorithm is provided with the s(r+1)-prefix of the target sequence. This assumption can be removed without altering the performance of the sequencing scheme.

Theorem 3 For constants $\gamma>1$ and $\beta=o(\log m)$, such that r and s are integers, let:

$$r = \frac{1}{\gamma}\log_4 m + \beta$$

$$s = \log_4 m + 1 + \gamma + r.$$

Let $\epsilon$ be the event: The algorithm fails to sequence a random string of length m using a GP(s,r) spectrum of the string. Then:

$$Pr(\epsilon) \leq 4^{-\gamma(1+\beta)}.$$

Proof:

Let $t=\{t,t_0, t_1, \ldots, t_r\}$, denote a vector of r+2 positions in the target string, and let $\mathcal{A}(t)$ denote the event: there are substrings in the target sequence $a_{(1,m)}$ that satisfy the following relations:

$a_{(t_0+1,t_0+s)} = a_{(t+1,t+s)}$     $\mathcal{B}_0(t)$ $a_{t_0+is} = a_{t+is}$, $2 \leq i \leq r$.     $\mathcal{C}_0(t)$ $a_{(t_0+(r+1)s)} \neq a_{(t+(r+1)s)}$     $\mathcal{D}_0(t)$ For $1 \leq j \leq r$ $a_{(t_j+1,t_j+s)} = a_{(t+js+1,t+(j+1)s)}$     $\mathcal{B}_j(t)$ $a_{t_j+is} = a_{t_{j-1}+(i+1)s}$, $2 \leq i \leq r$.     $\mathcal{C}_j(t)$ Focus first on the success of the algorithm in sequencing all but the last rs symbols of the target sequence.

Claim 1 The algorithm fails to sequence the m−sr prefix of the target string if and only if $\exists t$ such that $\mathcal{A}(t)$ occurs.

Proof: Assume that the algorithm is trying to extend the current sequence $b_{(1,l-1)}$ with the next symbol $b_l$. Let $t=l-s(r+1)$. If $|B_o|>1$ is not a singleton then there is a probe in the spectrum that matches $a_{(t+1,l-1)}$ but its rightmost symbol $b \neq a_l$. Denoting by $a_{(t_0+1,t_0+s(r+1))}$ the substring of the target string that binds with that probe, conditions $\mathcal{B}_0$, $\mathcal{C}_0$, and $\mathcal{D}_0$ hold.

If $\cap_{j=0}^{r} B_j$ is not a singleton, then it contains both $a_l$ and b. Thus, for each j there is a probe in the spectrum, and a corresponding substring $a_{(t_j+1,t_j+(r+1)s)}$ in the target sequence, such that the s-prefix of that substring matches $a_{(t+js+1,t+(j+1)s)}$, and the locations $t_j+is$ of the substring, for $2 \leq i \leq r$ match the corresponding locations (with a shift of s positions) of the substring $a_{(t_{j-1}+1,t_{j-1}+(r+1)s)}$ as formulated in conditions $\mathcal{B}_j$ and $\mathcal{C}_j$.

□

Let $\mathcal{T}$ denote the set of all possible vectors t, i.e.:

$$|\mathcal{T}| = \binom{m}{r+2}(r+2)!. \tag{1}$$

For a given vector $t \in$, let C(t) denote the set of components of t that are within a distance 3rs from any other component of t (in the following definition $t \equiv t_{-1}$):

$C(t) = \{j : \exists j' \neq j \text{ with } |t_{j'} - t_j| < 3rs\}$.

Let $\mathcal{T}_i$ denote the set of vectors with $|C(t)| = i$, i.e.:

$\mathcal{T}_i = \{t \in \mathcal{T} : |C(t)| = i\}$.

Next bound the probability of a given event $\mathcal{A}(t)$. If $t \in \mathcal{T}_0$ then the r+1 probes in the definition of $\mathcal{A}(t)$ are associated with disjoint regions of the string $a_{(1,m)}$, and thus the r+1 events are independent. If $t \in \mathcal{T}$ then all of the B events are still independent, and all but at most i of the C events are independent (a B event involves s+r−1 symbols (s+r for $B_0$), a C event r−1). Thus it is proved:

$$Pr(\mathcal{A}(t)) = 3 \times \left(\frac{1}{4}\right)^{(r+1)s+r^2} \quad t \in \mathcal{T}_0 \tag{2}$$

and $$Pr(\mathcal{A}(t)) \leq 3 \times \left(\frac{1}{4}\right)^{(r+1)s+r^2 - i(r-1)} \quad t \in \mathcal{T}_i \tag{3}$$

If $t \in \mathcal{T}_i$ then at least i of t's components are restricted to the 3rs−1-neighborhood of other r+2 components. Thus $$|\mathcal{T}_i| \leq |\mathcal{T}|\binom{r+1}{i}\left(\frac{6rs(r+2)}{m}\right)^i \tag{4}$$

$$\leq \binom{r+1}{i} m^{r+2}\left(\frac{6rs(r+2)}{m}\right)^i.$$

So, $$\sum_{a=1}^{r+1} |\mathcal{T}_a| \leq |\mathcal{T}| \sum_{a=1}^{r+1} \binom{r+1}{a}\left(\frac{6rs(r+2)}{m}\right)^a$$

$$= o(1).$$

Now bound the probability of an event $(\mathcal{A}(t))$ for $t \in \mathcal{T}_i$, $i \geq 1$:

$$Pr(\exists t \notin \mathcal{T}_0 : \mathcal{A}(t)) \leq \sum_{i=1}^{r+1} \binom{r+1}{i}(6rs(r+2))^i m^{r+2-i} 3\left(\frac{1}{4}\right)^{(r+1)s+r^2 - i(r-1)}$$

and $$= 3\frac{m^2}{4^{(\gamma+1)r+s}} \sum_{i=1}^{r+1} \binom{r+1}{i}\left(\frac{6rs(r+2)4^{r-1}}{m}\right)^i = o(1).$$

(This bound makes use of the condition $\beta = o(\log m)$ to get $4^r r^3 s \ll m$.)

Let I(t) be a binary variable such that I(t)=1 if and only if event $\mathcal{A}(t)$ occurs, and let $Z=\Sigma_{t \in T_0}I(t)$. Then $$Pr(\exists t \in T_0 : \mathcal{A}(t)) \leq E[Z].$$

Using (1) we get $$E(Z) \leq \binom{m}{r+2}(r+2)! \times 3 \times \left(\frac{1}{4}\right)^{(r+1)s+r^2}$$

$$\leq \frac{3m^2}{4^s r}\left(\frac{m}{4^{s+r}}\right)^r$$

$$\leq \frac{3m^2}{4^{s+(\gamma+1)r}}$$

$$\leq 3 \times 4^{-(\beta\gamma+\gamma+1)}$$

Thus, the probability that the algorithm fails to sequence all but the last rs symbols of the sequence is bounded from above by $$Pr(\exists t \notin T_0 : \mathcal{A}(t)) + Pr(\exists t \in T_0 : \mathcal{A}(t)) \leq o(1) + 3 \times 4^{-(1+\gamma(1+\beta))} \leq 4^{-\gamma(\beta+1)}.$$

Finally, if for all $m-rs < t < m$ it does not have the event $B_0(t) \cap C_0(t) \cap D_0(t)$ the last rs symbols are uniquely determined. But $$Pr\left(\bigcup_{j=m-rs}^{m}(B_0(t) \cap C_0(t) \cap D_0(t))\right) \leq rs 4^{-(r+s)} = o(1).$$

□

The procedure described and analyzed above, which involves (r+1) fooling probes shifted at regular intervals of s positions, will be briefly referred to as forward sequencing. The GS(s,r) spectrum, used in forward sequencing, can also be used for sequencing in reverse.

Let a denote a string over the alphabet $\{X,U\}$. By $FS_u(\alpha)$ we denote the sequence reconstruction process based on probes of type $\alpha$, whose confirmatory probes are shifted forward at regular intervals of u positions. By $RS_u(\alpha)$ we denote the analogous notion for sequencing in reverse. Two sequencing processes are equivalent ($\equiv$) if their respective events of the type $\mathcal{A}(t)$, defined in the proof of Theorem 3, are characterized by the same parameters and occur with the same probabilities. Starting from the standard pattern $X^1(U^{s-1}X)^r$, we shall establish:

1. $RS_1(X^s(U^{s-1}X)^r) \equiv FS_1(XU^{s-1})^r X^s)$.
2. $FS_1((XU^{s-1})^r X^s) \equiv FS_{r+1}(X^{r+1}(U^rX)^{s-1})$.

Statement 1 is immediate, since it simply corresponds to exchanging right-to-left shifts with left-to-right shifts. Statement 2 is established as follows. Represent a probing pattern by a 0–1 polynomial in the indeterminate x, where a term $x^j$ corresponds to an X-symbol in the (j+1)-st position (from the left).

$$\left[\text{Thus, } (XU^{s-1})^r X^s \text{ corresponds to the polynomial } p(x) = \right.$$

$$\left. \sum_{j=0}^{r-1} x^{js} + x^{rs}\sum_{i=0}^{s-1} x^i. \right]$$

Now subject the pattern to a "shuffle" rearrangement, denoted σ or, of its positions:

$$\sigma(i) = i(r+1) \mod ((r+1)s-1), \ \sigma((r+1)s-1) = (r+1)s-1),$$

and transform p(x) (mod $x^{(r+1)s-1}$) to $$\sum_{j=0}^{r-1}(x^{r+1})^{js} + (x^{r+1})^{rs}\sum_{i=0}^{s-2}(x^{r+1})^i = \sum_{j=0}^{r-1}x^j + x^r\sum_{i=0}^{s-2}x^{(r+1)i}.$$

The corresponding probe pattern $X^{r+1}(U^rX)^{s-1}$, appearing in Statement 2. In addition, a 1-position right-shift of the pattern $(XU^{s-1})^r X^s$, corresponds to an (r+1)-position right-shift of the pattern $X^r(U^rX)^{s-1}$. Since only a rearrangement of positions has been executed, the two processes are equivalent.

It can be observed that $X^{r+1}(U^rX)^{s-1}$ is a standard probing pattern used in a forward sequencing process. Thus, Theorem 3 fully applies, with the simple modification of interchanging parameters r and s−1, and it is presented that:

Theorem 4 For constant $\gamma > 1$ and $\beta = o(\log m)$, such that r and s are positive integers, let:

$$s = 1 + \frac{1}{\gamma}\log_4 m + \beta$$

$r = \log_4 m + 1 + \gamma - s$.

The algorithm fails to sequence in reverse a random string of length m using the GP(s,r) spectrum of the string with probability at most $4^{-\gamma(1+\beta)}$.

Removing the prefix requirements

The sequencing procedure outlined above requires a "seed" of length $s(r+1) = O((\log m)^2)$ symbols to "bootstrap" the process. Three solutions include, two biochemical and one algorithmic, to remove this requirement. The two biochemical methods are more practical.

If the SBH process is used to sequence one string of length m, the simplest solution is to synthesize a short "primer" (a string of length $O((\log m)^2)$) and attach it to the beginning of the string, thus providing the required prefix of the target string.

In most applications, however, one needs to sequence a string that is substantially longer than can be handled by SBH chips, even using our novel scheme. The standard solution is to fragment the target sequence by means of restriction enzymes to produce a collection of overlapping substrings of sizes that can be handled by the SBH method. Once each of the substrings is sequenced, standard techniques [W95] reconstruct the entire string. Since the substrings overlap, it is not necessary to sequence the beginning and the end of each substring. However, the algorithm with a seed sequence of length $O((\log m)^2)$ for each substring of length m is to be provided. This could be achieved by the following three steps: (1) Isolate a short, $O((\log m)^2)$, piece of the target sequence and sequence it using $O(4 \log \log m)$ solid (no gaps) probes (traditional method). (2) Use GP(s,r) probes for the forward sequencing of the portion of the target from the isolated piece to (almost) the end of the sequence. (3) Use the same set of GP(s,r) probes for the reverse sequencing of the portion from the isolated piece to the beginning of the sequence.

Finally, a purely combinatorial/algorithmic approach to remove the prefix requirement can be employed. A probe is selected at random or substantially at random from the spectrum and its unspecified positions (corresponding to the "don't care" gaps) are "filled" consistently with the spectrum. This results in a number of strings of length $s(r+1)+s-1=s(r+2)-1$, a subset of which correspond to actual substrings of the target sequence. Only these legitimate substrings are expected to be extensible by forward sequencing. Reverse sequencing of the terms that have been successfully extended in the forward direction, will complete the process. These techniques follow from principles in the art, including those described in [A+96] R. Arratia, D. Martin, G. Reinert and M. S. Waterman, Poisson process approximation for sequence repeats, and sequencing by hybridization, *Journal of Computational Biology* (1996) 3, 425–463;[BS91] W. Bains and G. C. Smith, A novel method for DNA sequence determination. *Jour. of Theoretical Biology* (1988), 135, 303–307; [DFS94] M. E. Dyer, A. M. Frieze, and S. Suen, The probability of unique solutions of sequencing by hybridization. *Journal of Computational Biology*, 1 (1994) 105–110; [D+89] R. Drmanac, I. Labat, I. Bruckner, and R. Crkvenjakov, Sequencing of megabase plus DNA by hybridization. *Genomics,* (1989),4, 114–128; [LB94] D. Loakes and D. M. Brown, 5-Nitroindole as a universal base analogue. *Nucleic Acids Research,* (1994), 22, 20,4039–4043; [L+88] Yu. P. Lysov, V. L. Florentiev, A. A. Khorlin, K. R. Khrapko, V. V. Shih, and A. D. Mirzabekov, Sequencing by hybridization via oligonlicleotides. A novel method, *Dokl. Acad. Sci. USSR,* (1988) 303, 1508–1511; [P89] P. A. Pevzner, 1-tuple DNA sequencing: computer analysis. *Journ. Biomolecul. Struct. & Dynamics* (1989) 7, 1, 63–73; [P+91] P. A. Pevzner, Yu. P. Lysov, K. R. Khrapko, A. V. Belyavsky, V. L. Florentiev, and A. D. Mirzabekov, Improved chips for sequencing by hybridization. *Journ. Biomolecul. Struct. & Dynamics* (1991) 9, 2, 399–410; [PL94] P. A. Pevzner and R. J. Lipshutz, Towards DNA-sequencing by hybridization. 19*th Symp. on Mathem. Found. of Comp, Sci.,* (1994), LNCS-841, 143–258; and [W95] M. S. Waterman, *Introduction to Computational Biology,* Chapman and Hall, 1995.

While the invention has been disclosed in connection with the embodiments shown and described in detail, various equivalents, modifications, and improvements will be apparent to one of ordinary skill in the art from the above description. Such equivalents, modifications, and improvements are intended to be encompassed by the following claims.

What is claimed is:

1. A method for sequencing a nucleic acid sequence, comprising providing a set of probes wherein each probe comprises an instance of a pattern of universal and designate nucleotides such that the set comprises a plurality of instances of the pattern, determining, in the set of probes a spectrum of probes which hybridize to a test sequence, and ordering the spectrum of probes to determine a sequence of a portion of the test sequence.

2. A method for ordering a spectrum of probes to determine a sequence of a portion of a test sequence, comprising i) providing a spectrum of probes that hybridize to a test sequence, wherein each probe in the spectrum is an instance of a pattern of universal and designate nucleotides, which pattern requires a designate nucleotide at an $m^{th}$ position and an $n^{th}$ position, ii) identifying a first subset of probes from the spectrum whose first m−1 nucleotides correspond to a last m−1 nucleotides of a growing sequence, iii) appending the nucleotide at the $m^{th}$ position to the growing sequence if a single nucleotide occurs at the $m^{th}$ position of all probes in the first subset.

3. The method of claim 2, further comprising iv) if two or more nucleotides occur at the $m^{th}$ position of the probes in the first subset, designating a new growing sequence for each of the nucleotides which occur at the $m^{th}$ position of the probes in the first subset, and v) repeating the steps of identifying and appending for each new growing sequence until the step of identifying identifies zero probes.

4. The method of claim 3, further comprising vi) if two or more nucleotides occur at the $m^{th}$ position of the probes in the first subset, selecting a second subset of probes from the spectrum whose first n−1 nucleotides correspond to a last n−1 nucleotides of the growing sequence, and vii) if a single nucleotide occurs at both the $m^{th}$ position of the probes in the first subset and the $n^{th}$ position of the probes in the second subset, appending the single nucleotide to the growing sequence.

5. The method of claim 4, further comprising viii) if two or more nucleotides occur at the $m^{th}$ position of the probes in the first subset and at the $n^{th}$ position of the probes in the second subset, designating a new growing sequence for each of the nucleotides which occur at the $m^{th}$ position of the probes in the first subset and at the $n^{th}$ position of the probes in the second subset, and ix) repeating steps ii) to v) for each new growing sequence until the step of identifying identifies zero probes.

* * * * *